United States Patent [19]

Hewett et al.

[11] Patent Number: 5,416,061
[45] Date of Patent: May 16, 1995

[54] HERBICIDAL COMBINATIONS OF BROMOXYNIL WITH SELECTED 2-BENZOYLCYCLOHEXANE-1,3-DIONES

[75] Inventors: Richard H. Hewett; Brian M. Luscombe, both of Ongar, England

[73] Assignee: Rhone-Poulenc Agriculture Ltd, Essex, England

[21] Appl. No.: 163,830

[22] Filed: Dec. 9, 1993

Related U.S. Application Data

[63] Continuation of Ser. No. 867,522, Apr. 13, 1992, abandoned.

[30] Foreign Application Priority Data

Apr. 17, 1991 [GB] United Kingdom ............... 9108199

[51] Int. Cl.[6] ...................... A01N 37/34; A01N 35/06
[52] U.S. Cl. .................... 504/141; 504/118; 504/310; 504/348
[58] Field of Search ............... 504/141, 118, 310, 348

[56] References Cited

U.S. PATENT DOCUMENTS

| H1,103 | 9/1992 | Decor et al. | 71/94 |
|---|---|---|---|
| 3,397,054 | 8/1968 | Hart et al. | 71/105 |
| 3,933,462 | 1/1976 | Fischer | 71/91 |
| 4,637,830 | 1/1987 | Dyer et al. | 71/105 |
| 4,759,794 | 7/1988 | Hsu | 71/93 |
| 4,780,127 | 10/1988 | Michaely et al. | 71/103 |
| 5,006,158 | 1/1991 | Carter et al. | 71/98 |
| 5,021,083 | 6/1991 | Schapira et al. | 71/105 |
| 5,080,709 | 1/1992 | Schumacher et al. | 71/88 |
| 5,149,358 | 9/1992 | Bernard | 71/92 |

FOREIGN PATENT DOCUMENTS

| 0064478 | 11/1982 | European Pat. Off. . |
|---|---|---|
| 0230596 | 8/1987 | European Pat. Off. . |
| 0306376 | 3/1989 | European Pat. Off. . |
| 0347950 | 12/1989 | European Pat. Off. . |
| 2126897 | 4/1984 | United Kingdom . |

OTHER PUBLICATIONS

Beraud et al, *Proceedings of the Brighton Crop Protection Conference, Weeds*-1991, vol. 1, pp. 51–56, Nov. 18–21, 1991.

Schulz et al, *Federation of European Biochemical Societ-*
(List continued on next page.)

*Primary Examiner*—Richard L. Raymond
*Assistant Examiner*—B. Bembenick
*Attorney, Agent, or Firm*—Burns, Doane, Swecker & Mathis

[57] ABSTRACT

Herbicidal compositions comprising (a) bromoxynil and (b) a 2-benzoylcyclohexane-1,3-dione derivative of general formula I:

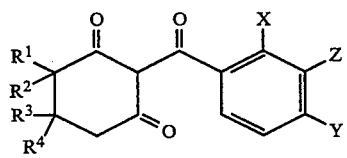

wherein
(i) Z represents the hydrogen atom;
  $R^1$ and $R^2$ which may be the same or different each represents the hydrogen atom or the methyl group,
  $R^3$ and $R^4$, which may be the same or different each represents the hydrogen atom or the methyl group,
  X represents the chlorine atom or the nitro group,
  Y represents the methylsulphonyl or trifluoromethyl group; or
(ii) Z represents the chlorine atom;
  $R^1$, $R^2$, $R^3$ and $R^4$ each represent the hydrogen atom,
  X represents the chlorine atom; and
  Y represents the methylsulphonyl group; salts thereof with agriculturally acceptable bases and their use in controlling weeds is described.

43 Claims, 12 Drawing Sheets

OTHER PUBLICATIONS

*ies,* vol. 318, No. 2, pp. 162–166, Mar. 1993.

*Weed Control Handbook: Principles,* ed. R. J. Hance, Blackwell Scientific Publications, eighth edition, Oxford, England, 280–281, 1990.

Limpel et al, *Proceedings of the North East Weed Control Conference,* 16 (1962), 48–53.

Tammes, *Neth. J. Plant. Path.* 70 (1964), 73–80.

O'Sullivan et al, *Weed Research,* vol. 20 (1980), 255–260.

Partyka et al, *Res. Rep. Expert Comm. Weeds West. Can.,* vol. 1 (1984), 233–234.

Milligan, *Res. Rep. Expert Comm. Weeds West. Can.,* vol. 2, (1985), 768.

McMullan et al, *Res. Rep. Expert Comm. Weeds West. Can.,* vol. 2 (1989), 756–757.

Code et al, *Res. Rep. Expert Comm. Weeds East. Can.* vol. 1 (1989), 106.

Hunter, *Res. Rep. Expert Comm. Weeds West. Can.,* vol. 1 (1986), 569.

HERBICIDAL COMBINATIONS OF BROMOXYNIL WITH SELECTED 2-BENZOYLCYCLOHEXANE-1,3-DIONES

This application is a continuation of application Ser. No. 07/867,522, filed Apr. 13, 1992, abandoned.

The present invention relates to a method of controlling the growth of weeds by the application of bromoxynil or an agriculturally acceptable salt or ester thereof and certain 2-benzoylcyclohexane-1,3-diones or agriculturally acceptable salts thereof, and to compositions containing them.

The 2-benzoylcyclohexane-1,3-dione derivatives used in the present invention are of general formula I:

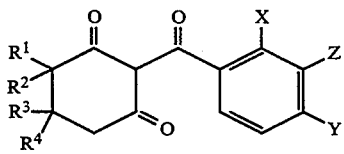

wherein
(i) Z represents the hydrogen atom;
$R^1$ and $R^2$ which may be the same or different, each represents the hydrogen atom or the methyl group,
$R^3$ and $R^4$ which may be the same or different, each represents the hydrogen atom or the methyl group,
X represents the chlorine atom or the nitro group,
Y represents the methylsulphonyl or trifluoromethyl group; or
(ii) Z represents the chlorine atom;
$R^1$, $R^2$, $R^3$ and $R^4$ each represent the hydrogen atom,
X represents the chlorine atom; and
Y represents the methylsulphonyl group; and salts thereof with agriculturally acceptable bases [which are embraced by the general formulae in the specifications of European Patent Publications No. 135191, 137963 and 186118 describing pre- and/or post emergence herbicides].

In certain cases the groups $R^1$, $R^2$, $R^3$ and $R^4$ contribute to optical and/or stereoisomerism. All such forms are embraced by the present invention.

The compounds of general formula I include
A. 2-(2-chloro-4-methylsulphonylbenzoyl)cyclohexane-1,3-dione
B. 2-(2-chloro-4-methylsulphonylbenzoyl)-5,5-dimethylcyclohexane-1,3-dione
C. 2-(2-chloro-4-methylsulphonylbenzoyl)-4,4-dimethylcyclohexane-1,3-dione
D. 2-(4-methylsulphonyl-2-nitrobenzoyl)cyclohexane-1,3-dione
E. 2-(2-nitro-4-trifluoromethylbenzoyl)cyclohexane-1,3-dione
F. 2-(2-chloro-4-trifluoromethylbenzoyl)cyclohexane-1,3-dione
G. 2-(4-methylsulphonyl-2-nitrobenzoyl)-5,5-dimethylcyclohexane-1,3-dione
H. 2-(2-nitro-4-trifluoromethylbenzoyl)-5,5-dimethylcyclohexane-1,3-dione
I. 2-(2-nitro-4-trifluoromethylbenzoyl)-4,4-dimethylcyclohexane-1,3-dione
J. 2-(4-methylsulphonyl-2-nitrobenzoyl)-4,4-dimethylcyclohexane-1,3-dione
K. 2-(2-nitro-4-trifluoromethylbenzoyl)-5-methylcyclohexane-1,3-dione
L. 2-(2-chloro-4-methylsulphonylbenzoyl)-5-methylcyclohexane-1,3-dione
M. 2-(2-nitro-4-methylsulphonylbenzoyl)-5-methylcyclohexane-1,3-dione
N. 2-(2,3-dichloro-4-methylsulphonylbenzoyl)cyclohexane-1,3-dione The letters are assigned to the above compounds for identification and reference hereinafter.

Bromoxynil [3,5-dibromo-4-hydroxybenzonitrile] may be used for post-emergence weed control in maize, wheat and barley. Although giving control of a wide range of broad-leaf weeds, control of some important species for example *Amaranthus retroflexus*, *Ipomoea purpurea* and *Sida spinosa* is unreliable. Owing to a lack of residual activity in the soil bromoxynil does not control the weeds which emerge after application. Bromoxynil has no useful activity against grass or sedge weeds.

It is to be understood that where in this specification reference is made to "bromoxynil" it is intended to refer, where the context so permits, to bromoxynil [3,5-dibromo-4-hydroxybenzonitrile] in the form of the parent phenol (acid equivalent: a.e.), or an agriculturally acceptable salt or ester thereof, preferably a metal or amine salt or an ester thereof with an alkanoic acid conreining from 2 to 10 carbon atoms.

As a result of research and experimentation it has now been discovered that the use of 2-benzoylcyclohexane-1,3-dione derivatives in combination with bromoxynil add to its capabilities of controlling a wide spectrum of broad-leaf weeds, grasses and sedges by both foliar activity and residual soil activity.

In addition to this it has been found that the combined herbicidal activity of combinations of 2-benzoylcyclohexane-1,3-dione derivatives with bromoxynil against certain species is greater than expected when applied post-emergence (e.g. as a post-emergence spray) i.e. the herbicidal activity of combinations of 2-benzoylcyclohexane-1,3-dione derivatives with bromoxynil showed on unexpected degree of synergism (as defined either by P. M. L. Tammes, Netherlands Journal of Plant Pathology, 70 (1964), pp 73–80 in a paper entitled "Isoboles, a graphic representation of synergism in pesticides", and by L. E. Limpel et al., Proceedings of the North East Weed Control Conference, 16 (1962), pp 48–53 in a paper entitled "Weed Control by dimethyl tetrachloro terephthalate alone and in certain mixtures".

The remarkable synergistic effect gives improved reliability of control of a number of weed species and allows for a reduction in the amount of active ingredients employed.

Accordingly the present invention provides a method for the control of the growth of weeds at a locus which comprises applying to the locus (a) bromoxynil and (b) a 2-benzoylcyclohexane-1,3-dione derivative of general formula I as hereinbefore defined or a salt thereof with an agriculturally acceptable base. For this purpose, the 2-benzoyl-cyclohexane-1,3-dione herbicide and bromoxynil are normally used in the form of herbicidal compositions (i.e. in association with compatible diluents or carriers and/or surface-active agents suitable for use in herbicidal compositions), for example as hereinafter described.

Preferred compounds of general formula I are those wherein
Z represents the hydrogen atom; and $R^3$ and $R^4$ both represent hydrogen atoms or both represent methyl groups.

Further preferred compounds of general formula I are those wherein $R^1$ and $R^2$ both represent hydrogen atoms or both represent methyl groups, and $R^3$ and $R^4$ both represent hydrogen atoms or both represent methyl groups.

The amounts of the 2-benzoyl-cyclohexane-1, 3-dione herbicide and bromoxynil applied vary with the nature of the weeds, the compositions used, the time of application, the climatic and edaphic conditions and (when used to control the growth of weeds in crop-growing areas) the nature of the crops. When applied to a crop-growing area, the rate of application should be sufficient to control the growth of weeds without causing substantial permanent damage to the crop. In general, taking these factors into account, application rates from 0.5 g to 500 g a.e. of the 2-benzoyl-cyclohexane-1,3-dione herbicide and from 2 g to 350 g a.e. of bromoxynil per hectare give good results. However, it is to be understood that higher or lower applications rates may be used, depending upon the particular problem of weed control encountered.

The cyclohexane herbicide and bromoxynil in combination may be used to control selectively the growth of weeds, for example to control the growth of those species hereinafter mentioned, by pre- or, preferably, post-emergence application in a directional or non-directional fashion e.g. by directional or non-directional spraying, to a locus of weed infestation which is an area used, or to be used, for growing crops, for example cereals, e.g. wheat, barley, oats, rye, maize and rice, soya beans, field and dwarf beans, peas, lucerne, cotton, peanuts, flax, onions, carrots, oilseed rape, sunflower, and permanent or sown grassland before or after sowing of the crop or before or after emergence of the crop. For the selective control of weeds at a locus of weed infestation which is an area used, or to be used, for the growing of crops, e.g. the crops hereinbefore mentioned, application rates from 25 g to 500 g a.e. of the 2-benzoylcyclohexane-1,3-dione herbicide and from 150 g to 350 g a.e. of bromoxynil per hectare are particularly suitable.

According to a feature of the present invention, there is provided a method for the control of the growth of weeds at a maize, wheat or barley crop locus which comprises applying to the locus (a) bromoxynil and (b) a 2-benzoylcyclohexane-1,3-dione derivative of general formula I as hereinbefore defined or a salt thereof with an agriculturally acceptable base. Preferably the application rates of (a) and (b) are from 2 to 350 preferably from 150 to 350 (more preferably from 200 to 300)g a.e./ha and from 0.5 to 500 and preferably from 25 to 500 more preferably 50 to 400 (for example 50 to 250)g acid equivalent/ha respectively in proportions of 700:1 to 1:250, preferably 14:1 to 1:3.33, more preferably 6:1 to 1:2 and more preferably 6:1 to 1:1.25 wt/wt of acid equivalent (a) to acid equivalent (b).

This method may be used to control a broad spectrum of weed species in maize, wheat and barley crops by post-emergence application without significant permanent damage to the crop. The combined use described above provides both foliar and residual activity.

By the term 'pre-emergence application' is meant application to the soil in which the weed seeds or seedlings are present before emergence of the weeds above the surface of the soil. By the term 'post-emergence application' is meant application to the aerial or exposed portions of the weeds which have emerged above the surface of the soil. By the term 'foliar activity' is meant herbicidal activity produced by application to the aerial or exposed portions of the weeds which have emerged above the surface of the soil. By the term 'residual activity' is meant herbicidal activity produced by application to the soil in which weed seeds or seedlings are present before emergence of the weeds above the surface of the soil, whereby seedlings present at the time of application or which germinate subsequent to application from seeds present in the soil are controlled.

Weeds that may be controlled by the method include: from broad-leaf weeds, *Abutilon theophrasti, Amaranthus retroflexus, Ambrosia trifida, Amsinckia intermedia, Anthemis arvensis, Bidens pilosa, Brassica kaber, Chenopodium album, Ipomoea spp* (e.g. *I. hederacea, I. pupurea*), *Kochia scoparia, Matricaria spp. Polygonum spp.* (e.g. *P. aviculare, P. convolvulus, P. pennsylvanicum, P. Persicaria, P. scabrum*), *Raphanus raphanistrum, Sesbania exaltata, Sida spinosa, Solanum spp.* (e.g. *S. elaeaquifolium, S. nigrum, S. nostratum, S. sarachoides*), *Sonchus oleraceus, Stellaria media, Thlaspi arvense, Xanthium pennsylvanicum*, and from grass weeds, *Digitaria sanguinalis, Echinochloa crus-galli* and *Eleusine indica*, and from sedges, *Cyperus spp.* (e.g. *C. esculentus* and *C. rotundus*).

In accordance with usual practice, a tank mix may be prepared prior to use by combining separate formulations of the individual herbicidal components, or separate formulations may be applied in a time-separated manner.

Figure 1:
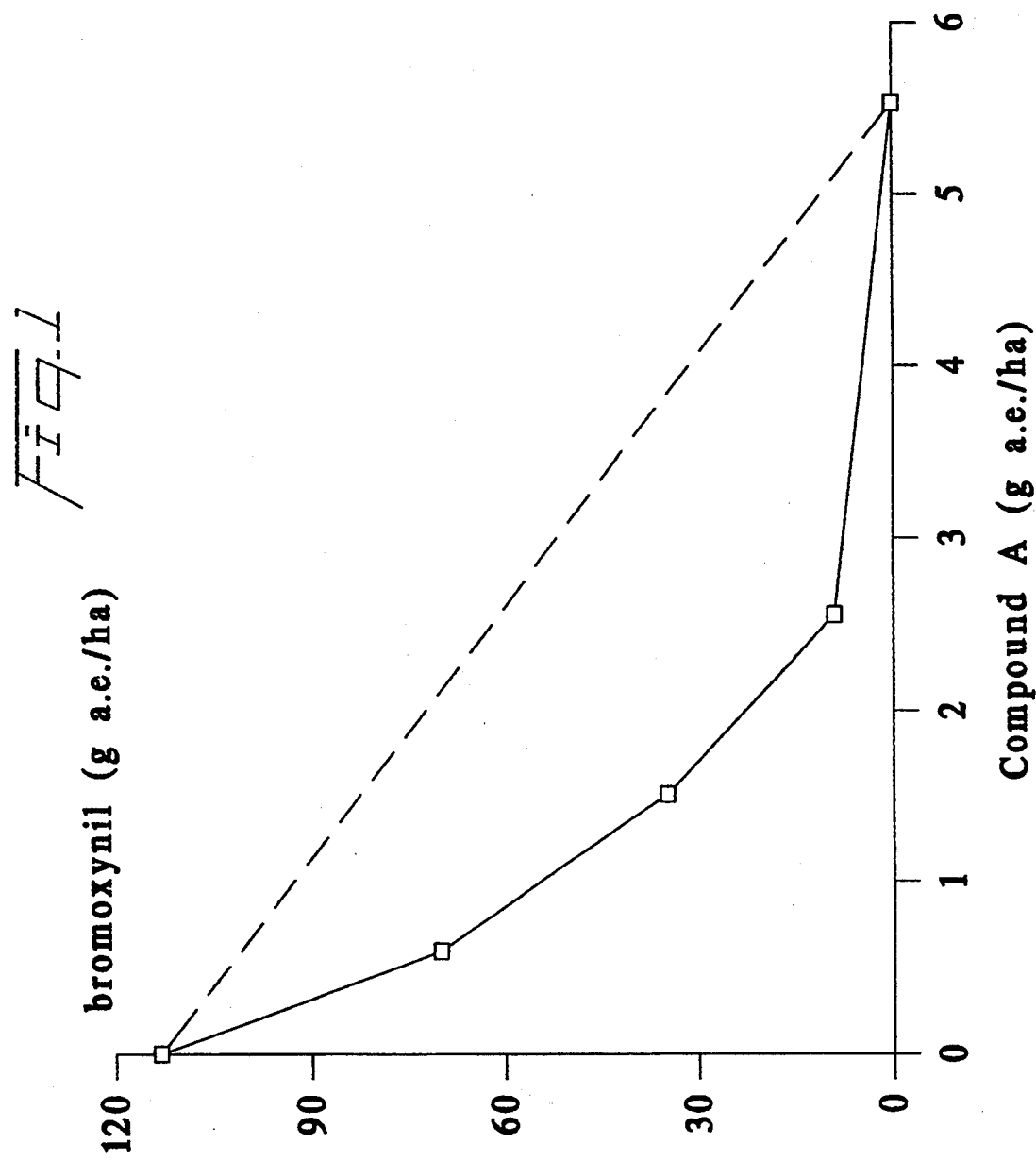
FIG. 1 is an ED50 isobole plot calculated from observed values (-□-) and a corresponding plot of expected additive values (—) for mixtures of Compound A with bromoxynil applied to *Abutilon theophrasti* seedlings.

The following experiments illustrate the present invention by demonstrating the synergistic activity of bromoxynil and 2-benzoylcyclohexane-1,3-dione derivatives.

EXPERIMENT 1

Glasshouse experiment showing biological synergism between bromoxynil and 2-(2-cholor-4-methylsulphonylbenzoyl)cyclohexane-1,3-dione [Compound A].

A wide range of doses of bromoxynil i.e. 9, 18, 35, 70 and 140 g a.e./ha (as technical phenol) and of 2-(2-chloro-4-methylsulphonylbenzoyl)cyclohexane-1, 3-dione i.e. 0.25, 0.5, 1, 2, 4, 8, 16, 31, 63 and 125 g a.e./ha (as technical material) were applied in acetone at a spray volume of 290 liter/ha to six replicate 7.5 cm square plastic plant pots of loam soil planted with 3 seedlings of *Abutilon theophrasti* at the 1 leaf stage or 3 seedlings of *Amaranthus retroflexus* at the 4 leaf stage, or 2 seedlings of *Brassica kaber* at the 2–3 leaf stage.

After spraying, the pots were arranged in randomised blocks in a glasshouse, and sub-irrigated. After 19 days the fresh weight of vegetation in each pot was determined. The mean fresh weights were used to calculate the percentage inhibition of each species thus:

$$\frac{\text{Mean weight in untreated pots} - \text{Mean weight in treated pots}}{\text{Mean weight in untreated pots}} \times 100.$$

Where possible the expected values (E) for treatments employing mixtures of the cyclohexanedione and bromoxynil were calculated from the results obtained with the components applied alone (X and Y) using the formula of Limpel et al (1962):

$$E = X + Y - \frac{XY}{100}$$

where E, X and Y are percentage inhibition of growth.

In addition, the ED 90 or ED 50 values (the application rates giving 90% and 50% inhibition of growth respectively) were calculated, as appropriate, from the results for the cyclohexanediones alone and with increasing rates of bromoxynil. The ED 90 or ED 50 values were then used to plot an isobole for each species.

The results of percentage inhibition of growth, the ED 90 or ED 50 values they represent and the calculated expected values for mixtures are given in Table I which follows:

TABLE I

| Application | rate (g a.e./ha) | % Inhibition of Growth | | | | | |
|---|---|---|---|---|---|---|---|
| Compound A | Bromoxynil | *Abutilon theophrasti* | | *Amaranthus retroflexus* | | *Brassica kaber* | |
| 2 | 0 | 33 | | 22 | | 0 | |
| 4 | 0 | 53 | | 25 | | 0 | |
| 8 | 0 | 64 | | 38 | | 1 | |
| 16 | 0 | 59 | | 46 | | 18 | |
| 31 | 0 | 66 | | 78 | | 68 | |
| 63 | 0 | 80 | | 93 | | 89 | |
| 125 | 0 | 86 | | 91 | | 98 | |
| | | ED50: 5.51 | | ED90: 76.25 | | ED90: 65.95 | |
| 0 | 9 | 17 | | 10 | | 45 | |
| 0 | 18 | 8 | | 58 | | 69 | |
| 0 | 35 | 26 | | 67 | | 61 | |
| 0 | 70 | 32 | | 68 | | 100 | |
| 0 | 140 | 52 | | 73 | | 100 | |
| | | ED50: 113.72 | | ED90: 138.15 | | ED90: 36.38 | |
| | | Observed | Expected | Observed | Expected | Observed | Expected |
| 1 | 9 | 22 | — | 41 | — | 53 | — |
| 2 | 9 | 41 | 44 | 74 | 30 | 84 | 45 |
| 4 | 9 | 75 | 59 | 73 | 33 | 89 | 45 |
| 8 | 9 | 80 | 68 | 76 | 44 | 100 | 46 |
| 16 | 9 | 86 | 64 | 95 | 51 | 93 | 55 |
| 31 | 9 | 89 | 70 | 100 | 80 | 97 | 82 |
| | | ED50: 2.55 | NA | ED90: 9.62 | NA | ED90: 2.58 | NA |
| 1 | 18 | 60 | — | 76 | — | 79 | — |
| 2 | 18 | 74 | 38 | 90 | 67 | 94 | 69 |
| 4 | 18 | 79 | 57 | 75 | 69 | 98 | 69 |
| 8 | 18 | 84 | 67 | 89 | 74 | 89 | 69 |
| 16 | 18 | 87 | 62 | 97 | 77 | 99 | 75 |
| | | ED50: <1 | NA | ED90: 4.18 | NA | ED90: 2.65 | NA |
| 0.5 | 35 | 18 | — | 71 | — | 88 | — |
| 1 | 35 | 52 | — | 71 | — | 100 | — |
| 2 | 35 | 58 | 50 | 87 | 74 | 100 | 61 |
| 4 | 35 | 81 | 65 | 99 | 75 | 99 | 61 |
| 8 | 35 | 76 | 73 | 95 | 80 | 98 | 61 |
| | | ED50: 1.50 | NA | ED90: 2.05 | NA | ED90: 0.52 | NA |

TABLE I-continued

| Application rate (g a.e./ha) | | % Inhibition of Growth | | | | | |
|---|---|---|---|---|---|---|---|
| Compound A | Bromoxynil | Abutilon theophrasti | | Amaranthus retroflexus | | Brassica kaber | |
| 0.25 | 70 | 34 | — | 65 | — | 100 | — |
| 0.5 | 70 | 44 | — | 72 | — | 99 | — |
| 1 | 70 | 57 | — | 91 | — | 100 | — |
| 2 | 70 | 76 | 54 | 88 | 75 | 100 | 100 |
| 4 | 70 | 86 | 68 | 93 | 76 | 98 | 100 |
| 8 | 70 | 92 | 76 | 97 | 80 | 94 | 100 |
| | | ED50: 0.59 | NA | ED90: 1.92 | NA | ED90: <0.25 | NA |

"—" Not calculated
"NA" Not applicable

Figure 2:
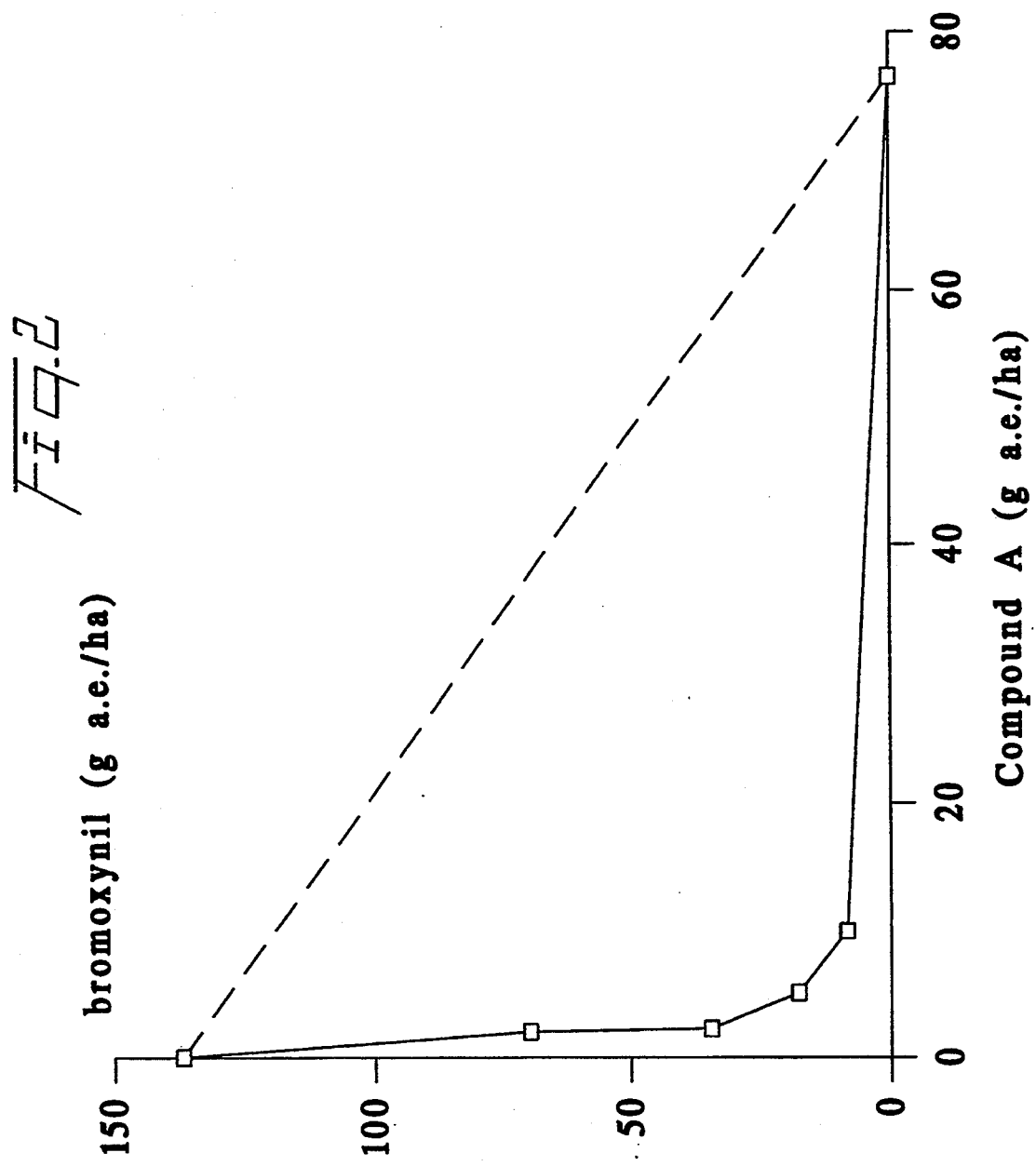
FIG. 2 is an ED90 isobole plot calculated from observed values (-□-) and a corresponding plot of expected additive values (—) for mixtures of Compound A with bromoxynil applied to *Amaranthus retroflexus* seedlings.
Figure 3:
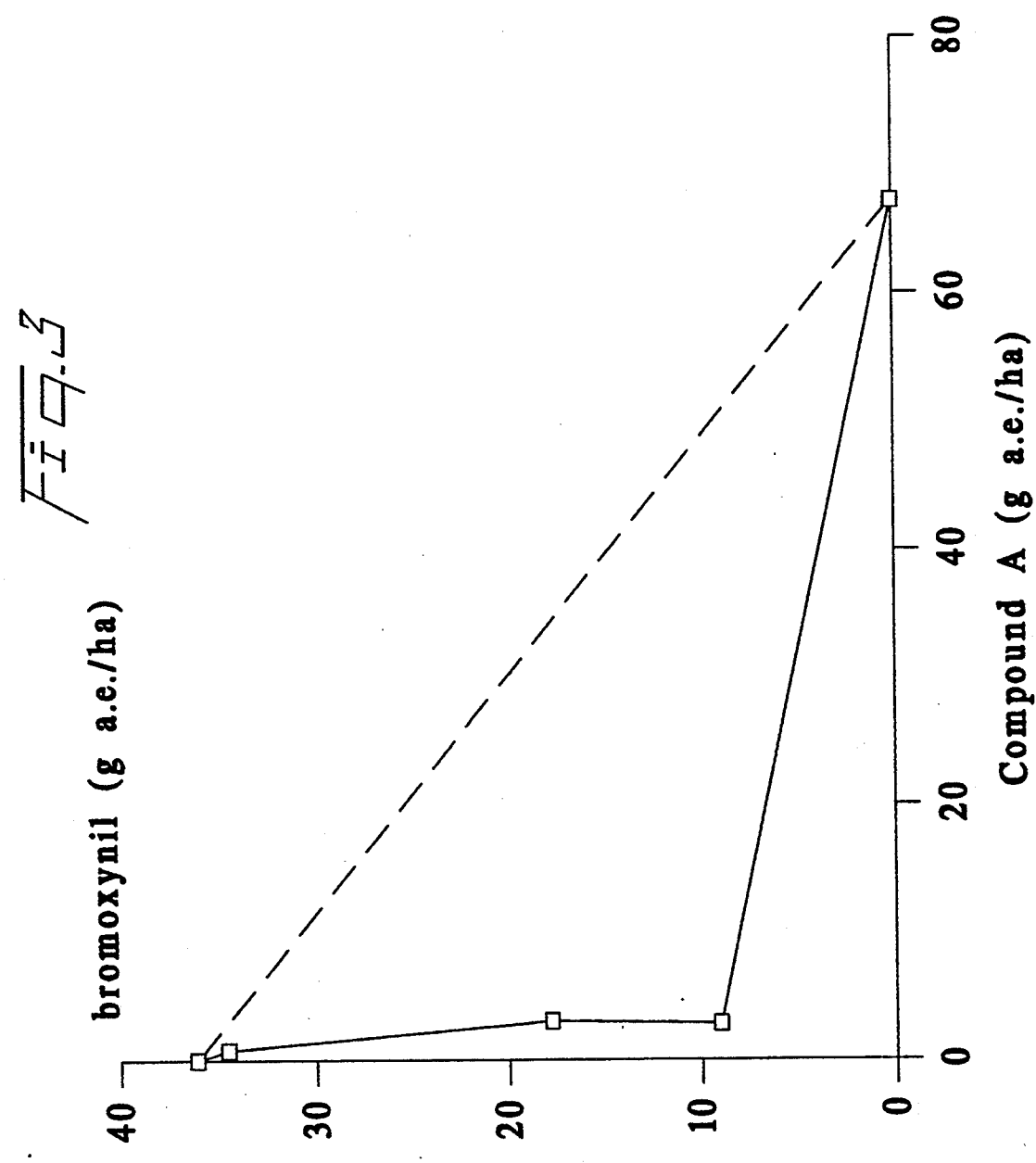
FIG. 3 is an ED90 isobole plot calculated from observed values (-□-) and a corresponding plot of expected additive values (—) for mixtures of Compound A with bromoxynil applied to *Brassica kaber* seedlings.
Figure 4:
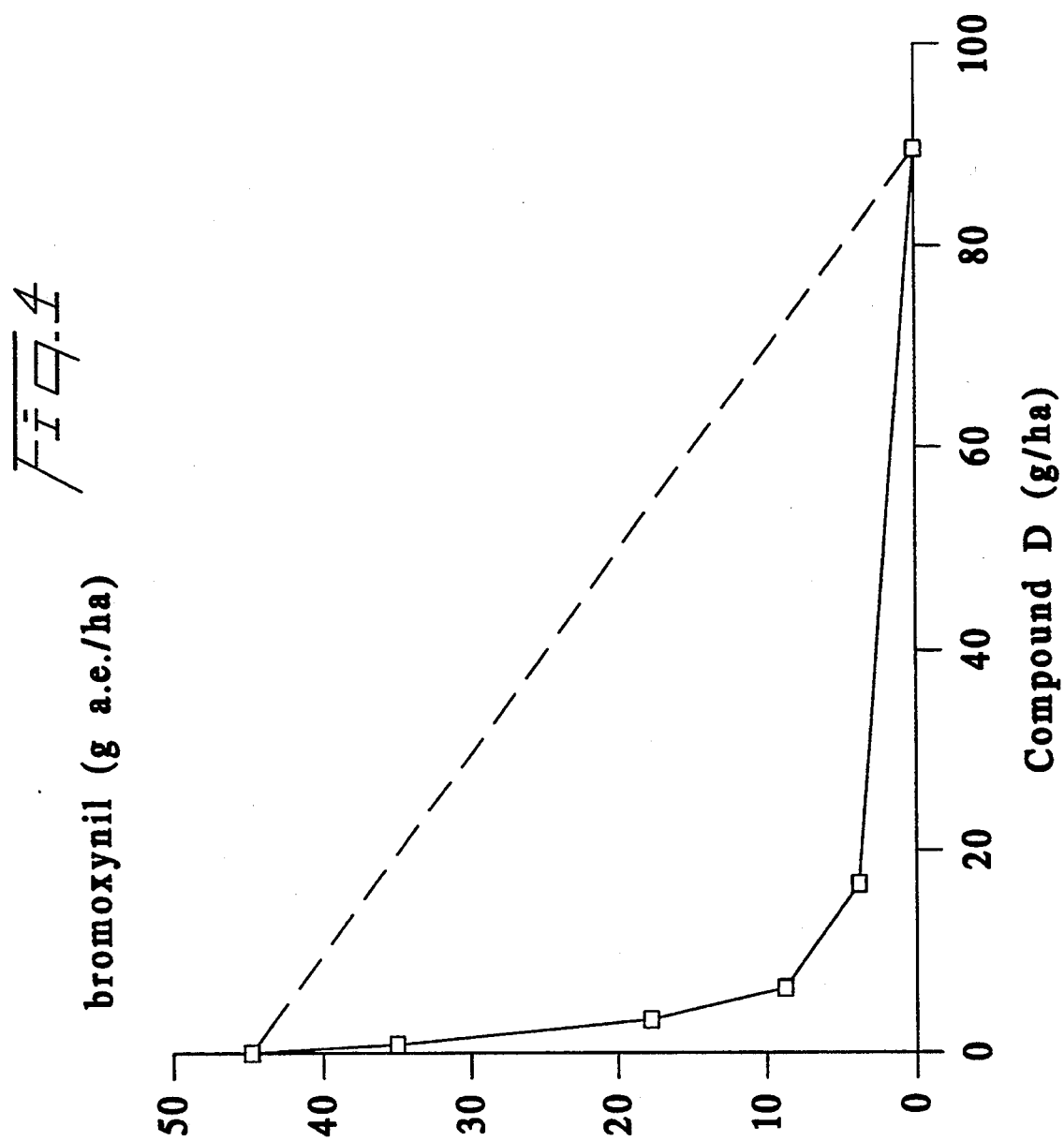
FIG. 4 is an ED90 isobole plot calculated from observed values (-□-) and a corresponding plot of expected additive values (—) for mixtures of Compound D with bromoxynil applied to Ipomoea species seedlings.
Figure 5:
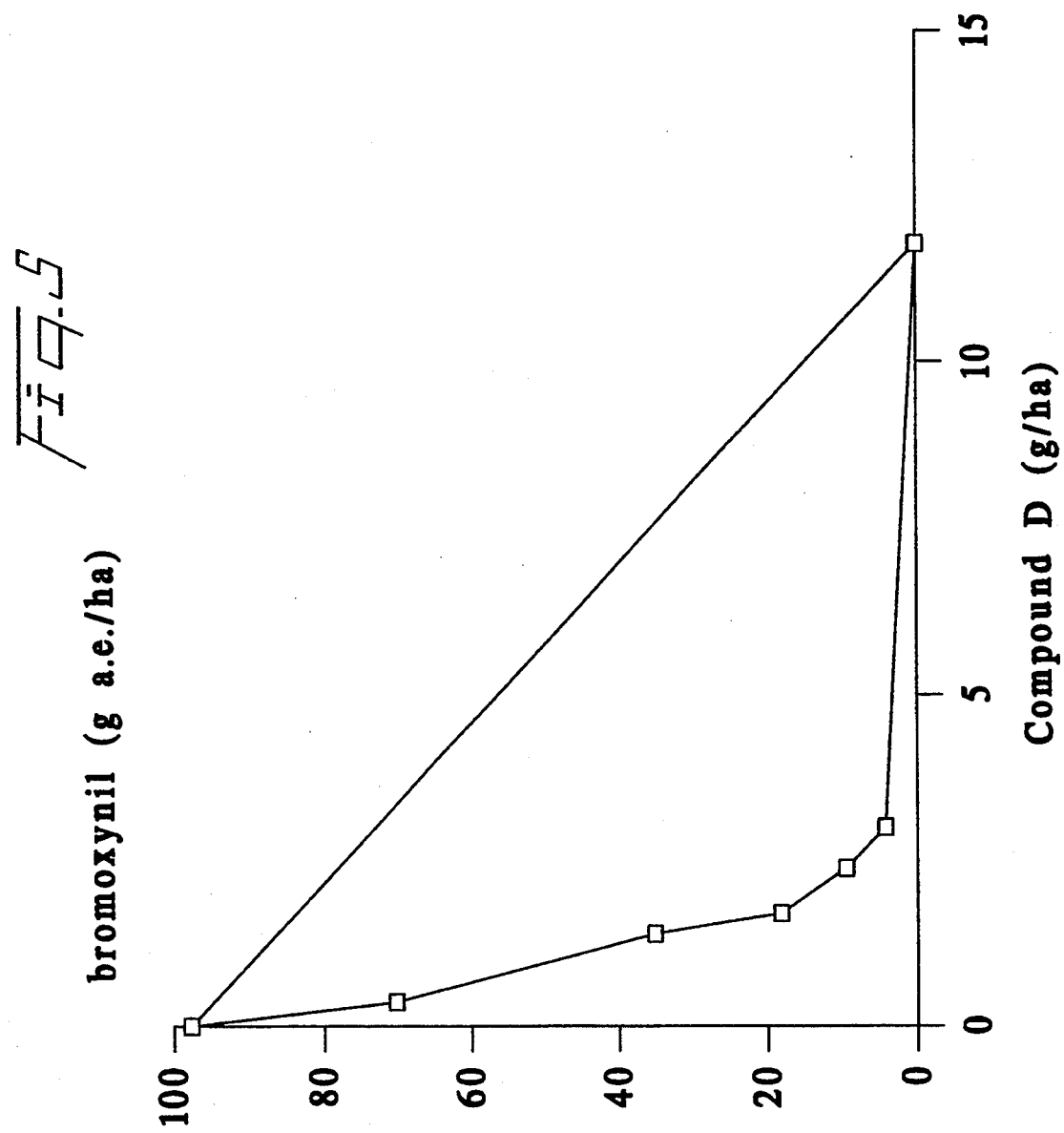
FIG. 5 is an ED50 isobole plot calculated from observed values (-□-) and a corresponding plot of expected additive values (—) for mixtures of Compound D with bromoxynil applied to *Echinochloa crus-galli* seedlings.
Figure 6:
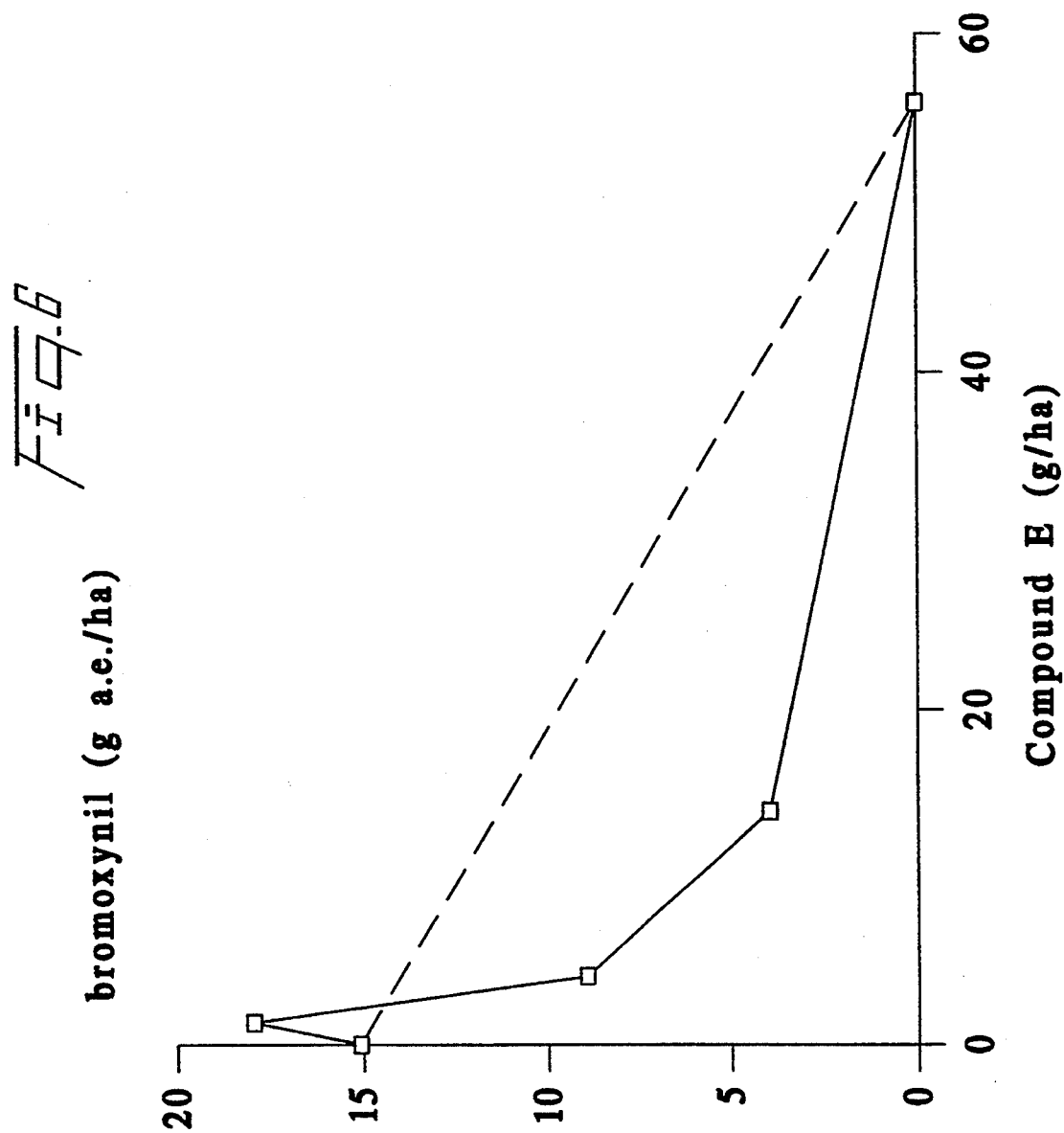
FIG. 6 is an ED50 isobole plot calculated from observed values (-□-) and a corresponding plot of expected additive values (—) for mixtures of Compound E with bromoxynil applied to Ipomoea species seedlings.
Figure 7:
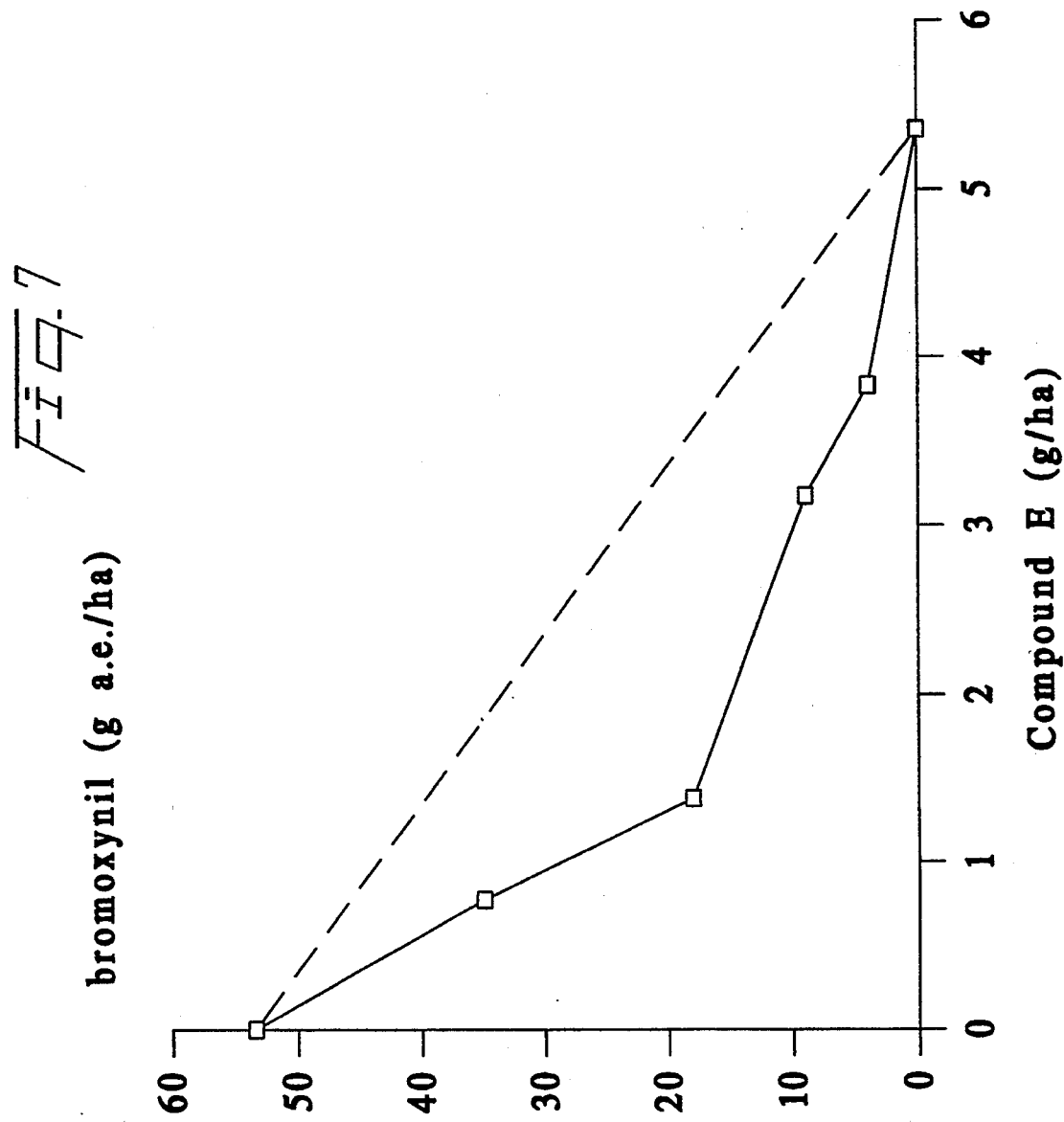
FIG. 7 is an ED50 isobole plot calculated from observed values (-□-) and a corresponding plot of expected additive values (—) for mixtures of Compound E with bromoxynil applied to *Sida spinosa* seedlings.

As the expected values are less than the values actually observed with mixtures, there is a clear demonstration of synergism. Also the isoboles produced, shown hereinafter in FIGS. 1, 2 and 3 were clearly type III curves (Tammes op.cit. Page 75, FIG. 2) characteristic of synergism.

EXPERIMENT 2

Glasshouse experiment showing biological synergism between bromoxynil and cyclohexane-1,3-dione derivatives.

A series of experiments were carried out to determine the nature of the biological interaction between bromoxynil and 2-cyclohexane-1,3-dione derivatives. The derivatives were compounds B, C, D, E, F, G, H, I, J, K, L, M and N. A wide range of dose rates of technical bromoxynil phenol and of the 2-benzoylcyclohexane-1,3-dione derivatives were applied in acetone at a spray volume of 290 l/ha to six replicate 7.5 cm square plastic plant pots of loam soil planted with seedlings of the target weed species. The dose rates of each component were selected according to the sensitivity of the weed species and are shown in the tables of results. The growth stages of the plants at spraying are also presented with the results.

After spraying the pots were arranged in randomised blocks in a glasshouse and sub-irrigated. After 19 days the fresh weight of vegetation in each pot was determined. The mean fresh weights were used to calculate the: percentage inhibition of each species as described in Experiment A.

The results of percentage inhibition of growth, appropriate ED90 and ED50 values they represent and the calculated expected values for the cyclohexanedione and bromoxynil mixtures are given in Tables II to X. In the tables that follow 'Ob' represents the observed results and 'Ex' represents the expected values for the various mixtures. The following abbreviations are used in the Tables:

ABUTH=*Abutilon threophrasti*
BIDPI=*Bidens pilosa*
DIGSA=*Digitaria sanguinalis*
ECHCG=*Echinochloa crus-galli*
ELEIN=*Eleusine indica*
IPOSS=Ipomoea species
SEBEX=*Sesbania exaltata*
SIDSP=*Sida spinosa*
SINAR=*Brassica kaber*

TABLE II

| Application rate (g/ha) | | % Inhibition of growth | | | | | |
|---|---|---|---|---|---|---|---|
| | | Bidens pilosa | | Brassica kaber | | Echinochloa crus-galli | |
| Compound B | Bromoxynil | Growth Stage | | | | | |
| | | 2 leaves | | 2–3 leaves | | 4 leaves | |
| 4 | 0 | 30 | | 31 | | 0 | |
| 8 | 0 | 46 | | 53 | | 18 | |
| 16 | 0 | 68 | | 81 | | 21 | |
| 31 | 0 | 69 | | 87 | | 24 | |
| 0 | 8 | 0 | | 21 | | 0 | |
| 0 | 16 | 44 | | 41 | | 0 | |
| 0 | 31 | 82 | | 78 | | 0 | |
| | | Ob | Ex | Ob | Ex | Ob | Ex |
| 4 | 8 | 32 | 30 | 75 | 45 | 19 | 0 |
| 8 | 8 | 65 | 46 | 81 | 62 | 11 | 18 |
| 16 | 8 | 81 | 68 | 78 | 85 | 26 | 21 |
| 31 | 8 | 87 | 69 | 83 | 90 | 33 | 24 |
| 4 | 16 | 52 | 60 | 90 | 60 | 0 | 0 |
| 8 | 16 | 74 | 70 | 90 | 72 | 35 | 18 |
| 16 | 16 | 73 | 82 | 90 | 89 | 37 | 21 |
| 31 | 16 | 86 | 82 | 100 | 93 | 36 | 24 |
| 4 | 31 | 75 | 87 | 94 | 85 | 30 | 0 |
| 8 | 31 | 92 | 90 | 96 | 89 | 43 | 18 |
| 16 | 31 | 98 | 94 | 100 | 96 | 40 | 21 |
| 31 | 31 | 96 | 94 | 93 | 97 | 66 | 24 |

TABLE III

| Application rate (g/ha) | | % Inhibition of growth | | | |
|---|---|---|---|---|---|
| | | Brassica kaber | | Digitaria sanguinalis | |
| Compound C | Bromoxynil | Growth Stage | | | |
| | | 2 leaves | | 3–4 leaves | |
| 1 | 0 | 14 | | 0 | |
| 2 | 0 | 18 | | 30 | |
| 4 | 0 | 34 | | 38 | |
| 8 | 0 | 71 | | 82 | |
| 0 | 8 | 42 | | 0 | |
| 0 | 16 | 71 | | 0 | |
| 0 | 31 | 92 | | 2 | |
| | | Ob | Ex | Ob | Ex |
| 1 | 8 | 67 | 50 | 13 | 0 |
| 2 | 8 | 88 | 52 | 23 | 30 |
| 4 | 8 | 94 | 62 | 62 | 38 |
| 8 | 8 | 99 | 83 | 71 | 82 |
| 1 | 16 | 93 | 75 | 17 | 0 |
| 2 | 16 | 97 | 76 | 42 | 30 |
| 4 | 16 | 97 | 81 | 61 | 38 |
| 8 | 16 | 99 | 92 | 87 | 82 |
| 1 | 31 | 97 | 93 | 18 | 2 |
| 2 | 31 | 95 | 93 | 44 | 31 |
| 4 | 31 | 100 | 95 | 55 | 39 |
| 8 | 31 | 98 | 98 | 92 | 82 |

TABLE IV

| Application rate (g/ha) | | % Inhibition of growth | |
|---|---|---|---|
| | | Ipomoea purpurea | Echinochloa crus-galli |
| Compound D | Bromoxynil | Growth Stage | |
| | | 1 leaf | 3 leaves |

TABLE IV-continued

| Application rate (g/ha) | | % Inhibition of growth | |
|---|---|---|---|
| | | *Ipomoea purpurea* | *Echinochloa crus-galli* |
| Compound D | Bromoxynil | Growth Stage | |
| 4 | 0 | 35 | 13 |
| 8 | 0 | 58 | 8 |
| 16 | 0 | 69 | 77 |
| 31 | 0 | 72 | 97 |
| 63 | 0 | 87 | 99 |
| 125 | 0 | 93 | 100 |
| | | $ED_{90}$ 89.46 | $ED_{50}$ 11.64 |
| 0 | 9 | 54 | 21 |
| 0 | 18 | 59 | 35 |
| 0 | 35 | 88 | 35 |
| 0 | 70 | 97 | 44 |
| 0 | 140 | 98 | 54 |
| | | $ED_{90}$ 44.31 | $ED_{50}$ 97.69 |
| | | Ob  Ex | Ob  Ex |
| 2 | 4 | 42  — | 30  — |
| 4 | 4 | 70  — | 63  — |
| 8 | 4 | 81  — | 91  — |
| 16 | 4 | 79  — | 98  — |
| 31 | 4 | 95  — | 98  — |
| 63 | 4 | 99  — | 99  — |
| | | $ED_{90}$ 16.64 | $ED_{50}$ 2.92 |
| | | IPOSS (1 leaf) | ECHCG (3 leaves) |
| | | Ob  Ex | Ob  Ex |
| 1 | 9 | 50  — | 34  — |
| 2 | 9 | 74  — | 43  — |
| 4 | 9 | 90  70 | 58  31 |
| 8 | 9 | 94  81 | 76  27 |
| 16 | 9 | 93  86 | 93  82 |
| | | $ED_{90}$ 6.11 — | $ED_{50}$ 2.35 — |
| 0.5 | 18 | 65  — | 25  — |
| 1 | 18 | 78  — | 36  — |
| 2 | 18 | 82  — | 55  — |
| 4 | 18 | 92  73 | 62  43 |
| 8 | 18 | 96  83 | 86  40 |
| | | $ED_{90}$ 3.15 — | $ED_{50}$ 1.68 — |
| 0.25 | 35 | 83  — | 36  — |
| 0.5 | 35 | 85  — | 30  — |
| 1 | 35 | 92  — | 34  — |
| 2 | 35 | 96  — | 51  — |
| 4 | 35 | 97  92 | 70  43 |
| | | $ED_{90}$ 0.71 — | $ED_{50}$ 1.35 — |
| 0.25 | 70 | 98  — | 57  — |
| 0.5 | 70 | 94  — | 51  — |
| 1 | 70 | 97  — | 58  — |
| 2 | 70 | 98  — | 70  — |
| 4 | 70 | 99  98 | 79  51 |
| | | $ED_{90}$ <0.25 — | $ED_{50}$ 0.33 — |

TABLE V

| Application rate (g/ha) | | % Inhibition of growth | | |
|---|---|---|---|---|
| | | *Ipomoea purpurea* | *Sida spinosa* | *Echinochloa crus-galli* |
| Compound E | Bromoxynil | 1 leaf | 1 leaf | 3 leaves |
| 8 | 0 | 5 | 64 | 84 |
| 16 | 0 | 21 | 71 | 95 |
| 31 | 0 | 31 | 84 | 97 |
| 63 | 0 | 61 | 95 | 98 |
| 125 | 0 | 65 | 97 | 99 |
| | | $ED_{50}$ 56.06 | $ED_{50}$ 5.35 | $ED_{90}$ 11.02 |
| 0 | 9 | 26 | 25 | 37 |
| 0 | 18 | 65 | 23 | 24 |
| 0 | 35 | 82 | 37 | 39 |
| 0 | 70 | 90 | 51 | 50 |
| 0 | 140 | 97 | 73 | 46 |
| | | $ED_{50}$ 15.14 | $ED_{50}$ 53.22 | $ED_{90}$ >140 |
| | | Ob  Ex | Ob  Ex | Ob  Ex |
| 4 | 4 | 26  — | 48  — | 56  — |
| 8 | 4 | 31  — | 74  — | 84  — |
| 16 | 4 | 45  — | 91  — | 97  — |
| 31 | 4 | 74  — | 97  — | 98  — |
| 63 | 4 | 84  — | 99  — | 100  — |
| | | $ED_{50}$ 13.98 | $ED_{50}$ 3.82 | $ED_{90}$ 12.38 |

TABLE V-continued

| Application rate (g/ha) | | % Inhibition of growth | | |
|---|---|---|---|---|
| | | *Ipomoea purpurea* | *Sida spinosa* | *Echinochloa crus-galli* |
| Compound E | Bromoxynil | 1 leaf | 1 leaf | 3 leaves |
| | | Ob  Ex | Ob  Ex | Ob  Ex |
| 2 | 9 | 52  — | 28  — | 71  — |
| 4 | 9 | 48  — | 72  — | 85  — |
| 8 | 9 | 49  30 | 75  73 | 91  90 |
| 16 | 9 | 83  42 | 95  78 | 97  97 |
| 31 | 9 | 88  49 | 97  88 | 99  98 |
| | | $ED_{50}$ 3.99 | $ED_{50}$ 3.16 | $ED_{90}$ 6.22 |
| 1 | 18 | 53  — | 33  — | 62  — |
| 2 | 18 | 79  — | 68  — | 68  — |
| 4 | 18 | 57  — | 85  — | 94  — |
| 8 | 18 | 90  67 | 94  72 | 93  88 |
| 16 | 18 | 86  72 | 98  78 | 98  96 |
| | | $ED_{50}$ 1.42 | $ED_{50}$ 1.37 | $ED_{90}$ 4.55 |
| 0.5 | 35 | 73  — | 36  — | 57  — |
| 1 | 35 | 84  — | 53  — | 69  — |
| 2 | 35 | 88  — | 85  — | 87  — |
| 4 | 35 | 95  — | 96  — | 96  — |
| 8 | 35 | 92  83 | 97  77 | 98  90 |
| | | $ED_{50}$ <0.5 | $ED_{50}$ 0.76 | $ED_{90}$ 2.44 |
| 0.5 | 70 | 98  — | 70  — | 50  — |
| 1 | 70 | 98  — | 81  — | 80  — |
| | | Ob  Ex | Ob  Ex | Ob  Ex |
| 2 | 70 | 89  — | 84  — | 90  — |
| 4 | 70 | 95  — | 95  — | 98  — |
| 8 | 70 | 97  90 | 97  82 | 99  92 |
| | | $ED_{50}$ <0.5 | $ED_{50}$ <0.5 | $ED_{90}$ 1.92 |

TABLE VI

| Application Rate (g/ha) | | % Inhibition of growth | | | |
|---|---|---|---|---|---|
| | | BIDPI (2 leaves) | SEBEX (2 leaves) | DIGSA (3 leaves) | ECHCG (4 leaves) |
| Cpd F | Bromoxynil | Ob  Ex | Ob  Ex | Ob  Ex | Ob  Ex |
| 16 | 0 | 4  — | 80  — | 19  — | 33  — |
| 31 | 0 | 24  — | 96  — | 25  — | 62  — |
| 63 | 0 | 33  — | 99  — | 45  — | 85  — |
| 125 | 0 | 51  — | 100  — | 55  — | 98  — |
| 8 | 0 | 18  — | 45  — | 8  — | 12  — |
| 16 | 0 | 64  — | 72  — | 14  — | 25  — |
| 32 | 0 | 96  — | 92  — | 11  — | 22  — |
| 16 | 8 | 64  22 | 94  89 | 9  26 | 36  42 |
| 31 | 8 | 59  38 | 99  98 | 14  31 | 63  67 |
| 63 | 8 | 85  46 | 100  99 | 20  49 | 86  86 |
| 125 | 8 | 79  60 | 100  100 | 39  59 | 99  98 |
| 16 | 16 | 87  66 | 97  94 | 19  30 | 47  50 |
| 31 | 16 | 95  73 | 100  99 | 41  35 | 67  72 |
| 63 | 16 | 95  76 | 100  100 | 35  52 | 92  88 |
| 125 | 16 | 97  83 | 100  100 | 41  61 | 97  98 |
| 16 | 31 | 97  96 | 97  98 | 12  28 | 44  48 |
| 31 | 31 | 100  97 | 100  100 | 11  33 | 77  71 |
| 63 | 31 | 100  97 | 100  100 | 37  51 | 90  88 |
| 125 | 31 | 99  98 | 100  100 | 47  60 | 98  98 |

TABLE VII

| Application rate (g/ha) | | % Inhibition of growth | | |
|---|---|---|---|---|
| | | *Bidens pilosa* | *Brassica kaber* | *Echinochloa crus-galli* |
| Compound G | Bromoxynil | 2 leaves | 2-3 leaves | 4 leaves |
| 4 | 0 | 32 | 62 | 0 |
| 8 | 0 | 55 | 85 | 0 |
| 16 | 0 | 64 | 95 | 11 |
| 31 | 0 | 80 | 97 | 2 |
| 0 | 8 | 0 | 21 | 0 |
| 0 | 16 | 44 | 41 | 0 |
| 0 | 31 | 82 | 78 | 0 |
| | | Ob  Ex | Ob  Ex | Ob  Ex |
| 4 | 8 | 32  32 | 92  70 | 0  0 |
| 8 | 8 | 76  55 | 100  88 | 3  0 |
| 16 | 8 | 92  64 | 99  96 | 22  11 |

TABLE VII-continued

| Application rate (g/ha) | | % Inhibition of growth | | | | | |
|---|---|---|---|---|---|---|---|
| | | *Bidens pilosa* | | *Brassica kaber* | | *Echinochloa crus-galli* | |
| Compound G | Bromoxynil | Growth Stage | | | | | |
| | | 2 leaves | | 2-3 leaves | | 4 leaves | |
| 31 | 8 | 98 | 80 | 100 | 97 | 29 | 2 |
| 4 | 16 | 78 | 61 | 100 | 78 | 12 | 0 |
| 8 | 16 | 97 | 74 | 99 | 91 | 21 | 0 |
| 16 | 16 | 96 | 80 | 100 | 97 | 10 | 11 |
| 31 | 16 | 98 | 89 | 100 | 98 | 41 | 2 |
| 4 | 31 | 95 | 87 | 100 | 91 | 8 | 0 |
| 8 | 31 | 98 | 92 | 100 | 97 | 27 | 0 |
| 16 | 31 | 98 | 93 | 99 | 99 | 44 | 11 |
| 31 | 31 | 99 | 96 | 100 | 99 | 39 | 2 |

TABLE VIII

| Application rate (g/ha) | | % Inhibition of growth | | | | | | | |
|---|---|---|---|---|---|---|---|---|---|
| | | SINAR (2 leaves) | | DIGSA (3-4 leaves) | | ECHCG (4 leaves) | | ELEIN (4 leaves) | |
| Cmpd H | Bromoxynil | Ob | Ex | Ob | Ex | Ob | Ex | Ob | Ex |
| 4 | 0 | 97 | — | 17 | — | 46 | — | 26 | — |
| 8 | 0 | 99 | — | 26 | — | 52 | — | 35 | — |
| 16 | 0 | 99 | — | 36 | — | 72 | — | 38 | — |
| 31 | 0 | 100 | — | 53 | — | 90 | — | 73 | — |
| 63 | 0 | 100 | — | 54 | — | 92 | — | 74 | — |
| 125 | 0 | 100 | — | 77 | — | 99 | — | 89 | — |
| 250 | 0 | 100 | — | 96 | — | 100 | — | 99 | — |
| | | | | ED 50 = 27.0 | | | | ED 50 = 16.1 | |
| 0 | 18 | 99 | — | 2 | — | 44 | — | 14 | — |
| 0 | 35 | 100 | — | 0 | — | 44 | — | 22 | — |
| 0 | 70 | 100 | — | 6 | — | 50 | — | 27 | — |
| 0 | 140 | 100 | — | 5 | — | 65 | — | 25 | — |
| 4 | 18 | 99 | 100 | 17 | 19 | 65 | 70 | 33 | 36 |
| 8 | 18 | 100 | 100 | 28 | 28 | 77 | 73 | 41 | 44 |
| 16 | 18 | 100 | 100 | 32 | 37 | 89 | 84 | 55 | 47 |
| 31 | 18 | 100 | 100 | 42 | 54 | 94 | 94 | 71 | 77 |
| 63 | 18 | 100 | 100 | 60 | 55 | 98 | 95 | 88 | 77 |
| 125 | 18 | 100 | 100 | 80 | 78 | 100 | 100 | 90 | 91 |
| | | | | ED 50 = 32.1 | | | | ED 50 = 10.8 | |
| 2 | 35 | 100 | 100 | 1 | — | 54 | — | 22 | — |
| 4 | 35 | 100 | 100 | 11 | 17 | 82 | 70 | 31 | 42 |
| 8 | 35 | 100 | 100 | 31 | 26 | 85 | 73 | 62 | 49 |
| 16 | 35 | 100 | 100 | 36 | 36 | 86 | 85 | 47 | 52 |
| 31 | 35 | 100 | 100 | 45 | 53 | 97 | 94 | 66 | 79 |
| 63 | 35 | 100 | 100 | 50 | 54 | 99 | 95 | 81 | 79 |
| | | | | ED 50 = 30.8 | | | | ED 50 = 10.3 | |
| 2 | 70 | 100 | — | 10 | — | 78 | — | 34 | — |
| 4 | 70 | 100 | 100 | 22 | 23 | 83 | 73 | 34 | 46 |
| 8 | 70 | 100 | 100 | 22 | 31 | 87 | 76 | 42 | 53 |
| 16 | 70 | 100 | 100 | 30 | 40 | 97 | 86 | 45 | 55 |
| 31 | 70 | 100 | 100 | 47 | 56 | 100 | 95 | 75 | 80 |
| 63 | 70 | 100 | 100 | 58 | 57 | 100 | 96 | 93 | 81 |
| | | | | ED 50 = 39.8 | | | | ED 50 = 8.7 | |
| 1 | 140 | 100 | — | 0 | — | 75 | — | 32 | — |
| 2 | 140 | 100 | — | 7 | — | 84 | — | 43 | — |
| 4 | 140 | 100 | 100 | 16 | 22 | 90 | 81 | 44 | 44 |
| 8 | 140 | 100 | 100 | 26 | 30 | 98 | 83 | 61 | 51 |
| 16 | 140 | 100 | 100 | 39 | 39 | 99 | 90 | 76 | 54 |
| 31 | 140 | 100 | 100 | 46 | 55 | 100 | 97 | 84 | 80 |
| | | | | ED 50 = 24.4 | | | | ED 50 = 3.6 | |

TABLE IX

| Application rate (g/ha) | | % Inhibition of growth *Echinochloa crus-galli* |
|---|---|---|
| Compound I | Bromoxynil | Growth stage-4 leaves |
| 4 | 0 | 29 |
| 8 | 0 | 49 |
| 16 | 0 | 65 |
| 31 | 0 | 78 |
| 63 | 0 | 90 |
| 125 | 0 | 91 |
| 250 | 0 | 95 |
| | | ED$_{90}$ 92.88 |
| 0 | 35 | 33 |
| 0 | 70 | 43 |
| 0 | 140 | 42 |
| | | ED$_{90}$ >140 |
| | | Observed / Expected |
| 2 | 35 | 41 / — |
| 4 | 35 | 66 / 52 |
| 8 | 35 | 70 / 66 |
| 16 | 35 | 81 / 77 |
| 31 | 35 | 90 / 85 |
| 63 | 35 | 94 / 93 |
| | | ED$_{90}$ 32.92 / — |
| 2 | 70 | 47 / — |
| 4 | 70 | 66 / 60 |
| 8 | 70 | 74 / 71 |
| 16 | 70 | 83 / 80 |
| 31 | 70 | 93 / 87 |
| 63 | 70 | 97 / 94 |
| | | ED$_{90}$ 22.98 / — |
| 1 | 140 | 57 / — |
| 2 | 140 | 68 / — |
| 4 | 140 | 78 / 59 |
| 8 | 140 | 85 / 70 |
| 16 | 140 | 90 / 80 |
| 31 | 140 | 95 / 87 |
| | | ED$_{90}$ 14.14 |

TABLE X

| Application rate (g/ha) | | % Inhibition of growth Brassica kaber | |
|---|---|---|---|
| Compound J | Bromoxynil | Growth stage 2 leaves | |
| 1 | 0 | 47 | |
| 2 | 0 | 60 | |
| 4 | 0 | 86 | |
| 8 | 0 | 95 | |
| 0 | 8 | 42 | |
| 0 | 16 | 71 | |
| 0 | 31 | 92 | |
| | | Observed | Expected |
| 1 | 8 | 70 | 69 |
| 2 | 8 | 93 | 77 |
| 4 | 8 | 97 | 92 |
| 8 | 8 | 100 | 97 |
| 1 | 16 | 90 | 85 |
| 2 | 16 | 99 | 88 |
| 4 | 16 | 99 | 96 |
| 8 | 16 | 100 | 99 |
| 1 | 31 | 99 | 96 |
| 2 | 31 | 98 | 97 |
| 4 | 31 | 100 | 99 |
| 8 | 31 | 100 | 100 |

TABLE XI

| Application rate (g/ha) | | % Inhibition of growth | | | |
|---|---|---|---|---|---|
| | | Bidens pilosa | | Echinochloa crus-galli | |
| | | Growth stage | | | |
| Compound K | Bromoxynil | 2 leaves | | 4 leaves | |
| 2 | 0 | 0 | | 53 | |
| 4 | 0 | 13 | | 74 | |
| 8 | 0 | 41 | | 82 | |
| 16 | 0 | 56 | | 93 | |
| 0 | 8 | 22 | | 0 | |
| 0 | 16 | 60 | | 12 | |
| 0 | 31 | 98 | | 16 | |
| | | Ob | Ex | Ob | Ex |
| 2 | 8 | 39 | 22 | 64 | 53 |
| 4 | 8 | 74 | 32 | 79 | 74 |
| 8 | 8 | 89 | 54 | 90 | 82 |
| 16 | 8 | 91 | 66 | 97 | 93 |
| 2 | 16 | 68 | 60 | 64 | 58 |
| 4 | 16 | 88 | 65 | 87 | 77 |
| 8 | 16 | 94 | 76 | 90 | 84 |
| 16 | 16 | 96 | 83 | 92 | 94 |
| 2 | 31 | 99 | 98 | 83 | 61 |
| 4 | 31 | 100 | 98 | 87 | 78 |
| 8 | 31 | 97 | 99 | 88 | 85 |
| 16 | 31 | 99 | 99 | 97 | 94 |

TABLE XII

| Application rate (g/ha) | | % Inhibition of growth | | | | | |
|---|---|---|---|---|---|---|---|
| Compound L | Bromoxynil | BIDPI (2 leaves) | | SIDSP (1–2 leaves) | | ECHCG (4 leaves) | |
| 2 | 0 | 0 | | 0 | | 61 | |
| 4 | 0 | 2 | | 0 | | 68 | |
| 8 | 0 | 9 | | 0 | | 85 | |
| 16 | 0 | 17 | | 5 | | 93 | |
| 0 | 8 | 22 | | 0 | | 0 | |
| 0 | 16 | 60 | | 28 | | 12 | |
| 0 | 31 | 98 | | 52 | | 16 | |
| | | Ob | Ex | Ob | Ex | Ob | Ex |
| 2 | 8 | 50 | 22 | 0 | 0 | 62 | 61 |
| 4 | 8 | 41 | 24 | 1 | 0 | 85 | 69 |
| 8 | 8 | 68 | 29 | 14 | 0 | 83 | 85 |
| 16 | 8 | 72 | 35 | 46 | 5 | 96 | 93 |
| 2 | 16 | 59 | 60 | 0 | 28 | 61 | 65 |
| 4 | 16 | 82 | 61 | 25 | 28 | 87 | 72 |
| 8 | 16 | 85 | 64 | 33 | 28 | 93 | 87 |
| 16 | 16 | 92 | 67 | 55 | 32 | 98 | 94 |
| 2 | 31 | 96 | 98 | 45 | 52 | 73 | 67 |
| 4 | 31 | 97 | 98 | 64 | 52 | 87 | 73 |
| 8 | 31 | 99 | 98 | 73 | 52 | 95 | 87 |
| 16 | 31 | 98 | 98 | 74 | 54 | 98 | 94 |

TABLE XIII

| Application rate (g/ha) | | % Inhibition of growth | | |
|---|---|---|---|---|
| Compound M | Bromoxynil | BIDPI (2 leaves) | IPOSS (1 leaf) | ECHCG (3 leaves) |
| 4 | 0 | 0 | 28 | 20 |
| 8 | 0 | 0 | 6 | 21 |
| 16 | 0 | 0 | 8 | 20 |
| 31 | 0 | 4 | 20 | 49 |
| 63 | 0 | 0 | 20 | 74 |
| 125 | 0 | 25 | 34 | 75 |
| 250 | 0 | 50 | 38 | 96 |
| | | ED 50 > 219.5 | | ED 50 = 28.0 |
| 0 | 4 | 0 | 21 | 22 |
| 0 | 9 | 0 | 18 | 25 |
| 0 | 18 | 18 | 2 | 27 |
| 0 | 35 | 78 | 17 | 37 |
| 0 | 70 | 92 | 8 | 39 |
| 0 | 140 | 100 | 5 | 50 |
| | | ED 50 > 30.2 | | ED 50 = 154.8 |
| 2 | 4 | 0 | 0 | 14 |
| 4 | 4 | 0 | 7 | 30 |
| 8 | 4 | 0 | 0 | 28 |
| 16 | 4 | 1 | 17 | 40 |
| 31 | 4 | 10 | 9 | 44 |
| 63 | 4 | 28 | 22 | 88 |
| | | ED 50 > 63 | | ED 50 = 17.0 |
| 1 | 9 | 0 | 6 | 15 |
| 2 | 9 | 5 | 12 | 20 |
| 4 | 9 | 14 | 4 | 42 |
| 8 | 9 | 3 | 11 | 40 |
| 16 | 9 | 12 | 10 | 51 |
| 31 | 9 | 31 | 18 | 79 |
| | | ED 50 > 31 | | ED 50 = 9.2 |
| 0.5 | 18 | 19 | 26 | 20 |
| 1 | 18 | 12 | 16 | 25 |
| 2 | 18 | 7 | 15 | 35 |
| 4 | 18 | 29 | 12 | 40 |
| 8 | 18 | 29 | 20 | 47 |
| 16 | 18 | 45 | 28 | 49 |
| | | ED 50 = 15.7 | | ED 50 = 12.3 |
| 0.25 | 35 | 41 | 2 | 20 |
| 0.5 | 35 | 72 | 9 | 33 |
| 1 | 35 | 51 | 1 | 35 |
| 2 | 35 | 59 | 0 | 41 |
| 4 | 35 | 51 | 20 | 50 |
| 8 | 35 | 62 | 10 | 55 |
| | | ED 50 = 3.0 | | ED 50 = 4.4 |

TABLE XIV

| Application Rate (g/ha) | | % Inhibition of growth | | | |
|---|---|---|---|---|---|
| Compound N | Bromoxynil | ABUTH (2 lvs) | SIDSP (1 leaf) | DIGSA (4 lvs) | ECHCG (4 lvs) |
| 8 | 0 | 66 | 45 | 20 | 32 |
| 16 | 0 | 70 | 47 | 12 | 37 |
| 31 | 0 | 80 | 55 | 27 | 43 |
| 63 | 0 | 85 | 61 | 47 | 68 |
| 125 | 0 | 94 | 75 | 58 | 89 |
| 250 | 0 | 100 | 83 | 68 | 95 |
| ED 90 values: | | 58.8 | 18.0 | 84.4 | 25.2 |
| 0 | 18 | 31 | 23 | 3 | 27 |
| 0 | 35 | 24 | 35 | 5 | 31 |
| 0 | 70 | 89 | 33 | 8 | 42 |
| 0 | 140 | 100 | 29 | 8 | 44 |
| 0 | 280 | 98 | 41 | 17 | 51 |
| ED 90 values: | | 74.0 | 460 | 5934 | 227.5 |
| 4 | 18 | 94 | 34 | 11 | 45 |
| 8 | 18 | 97 | 61 | 16 | 50 |
| 16 | 18 | 98 | 60 | 23 | 57 |

TABLE XIV-continued

| Application Rate (g/ha) | | % Inhibition of growth | | | |
|---|---|---|---|---|---|
| Compound N | Bromoxynil | ABUTH (2 lvs) | SIDSP (1 leaf) | DIGSA (4 lvs) | ECHCG (4 lvs) |
| 31 | 18 | 99 | 75 | 29 | 77 |
| 63 | 18 | 98 | 82 | 47 | 93 |
| 125 | 18 | 100 | 87 | 50 | 94 |
| ED 90 values: | | <4 | 7.6 | 105.3 | 7.6 |
| 4 | 35 | 97 | 48 | 27 | 66 |
| 8 | 35 | 96 | 60 | 25 | 71 |
| 16 | 35 | 100 | 70 | 37 | 82 |
| 31 | 35 | 100 | 76 | 34 | 81 |
| 63 | 35 | 100 | 82 | 45 | 88 |
| 125 | 35 | 100 | 87 | 52 | 93 |
| ED 90 values: | | <4 | 3.9 | 101.8 | 1.2 |
| 2 | 70 | 99 | 53 | 13 | 52 |
| 4 | 70 | 100 | 75 | 31 | 68 |
| 8 | 70 | 100 | 64 | 23 | 75 |
| 16 | 70 | 100 | 80 | 40 | 89 |
| 31 | 70 | 100 | 84 | 34 | 90 |
| 63 | 70 | 100 | 87 | 48 | 91 |
| ED 90 values: | | <2 | 1.5 | 49.9 | 1.5 |
| 1 | 140 | 89 | 41 | 18 | 52 |
| 2 | 140 | 95 | 27 | 20 | 63 |
| 4 | 140 | 100 | 45 | 33 | 66 |
| 8 | 140 | 99 | 57 | 18 | 63 |
| 16 | 140 | 100 | 74 | 31 | 70 |
| 31 | 140 | 100 | 79 | 43 | 74 |
| ED 90 values: | | 1.1 | 4.4 | 40.2 | 0.6 |

The equation of Limpel could be applied to the data generated by this series of experiments on over 220 occasions. Of these, expected values were less than the values on the vast majority of occasions showing a clear demonstration of synergism.

Figure 8:
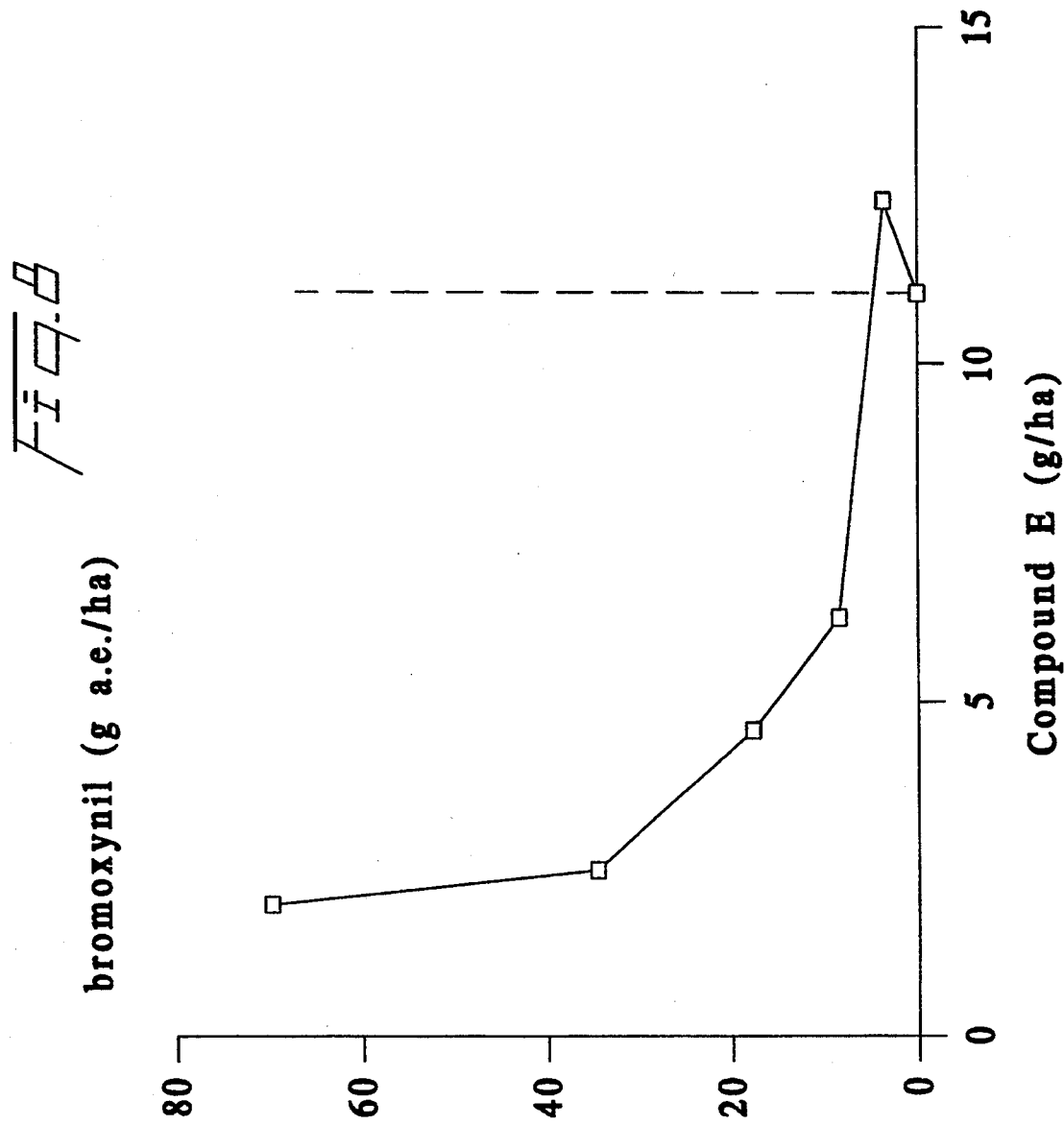
FIG. 8 is an ED90 isobole plot calculated from observed values (-□-) and a corresponding plot of expected additive values (—) for mixtures of Compound E with, bromoxynil applied to *Echinochloa crus-galli* seedlings.
Figure 9:
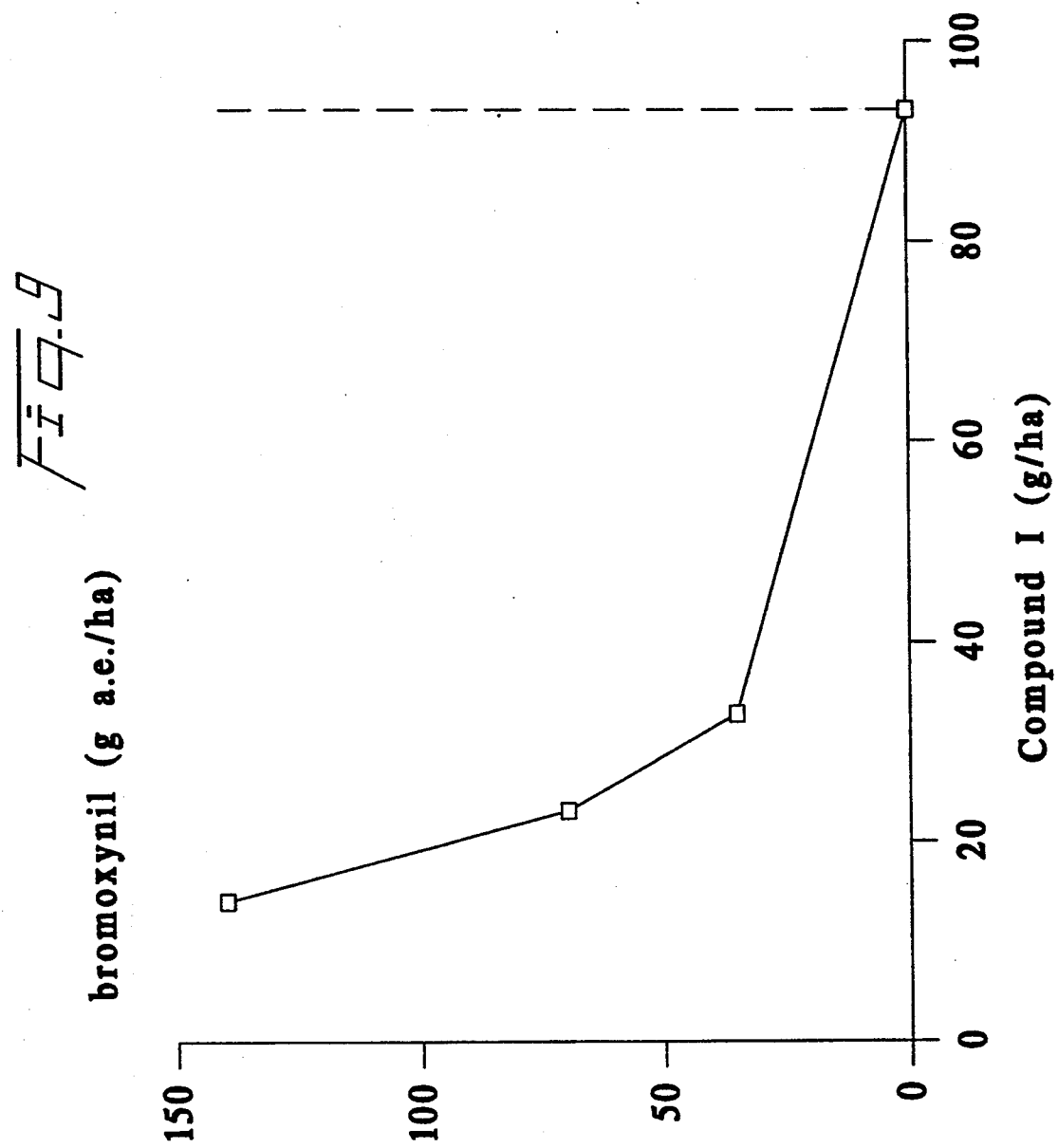
FIG. 9 is an ED90 isobole plot calculated from observed values (-□-) and a corresponding plot of expected additive values (—) for mixtures of Compound I with bromoxynil applied to *Echinochloa crus-galli* seedlings.
Figure 10:
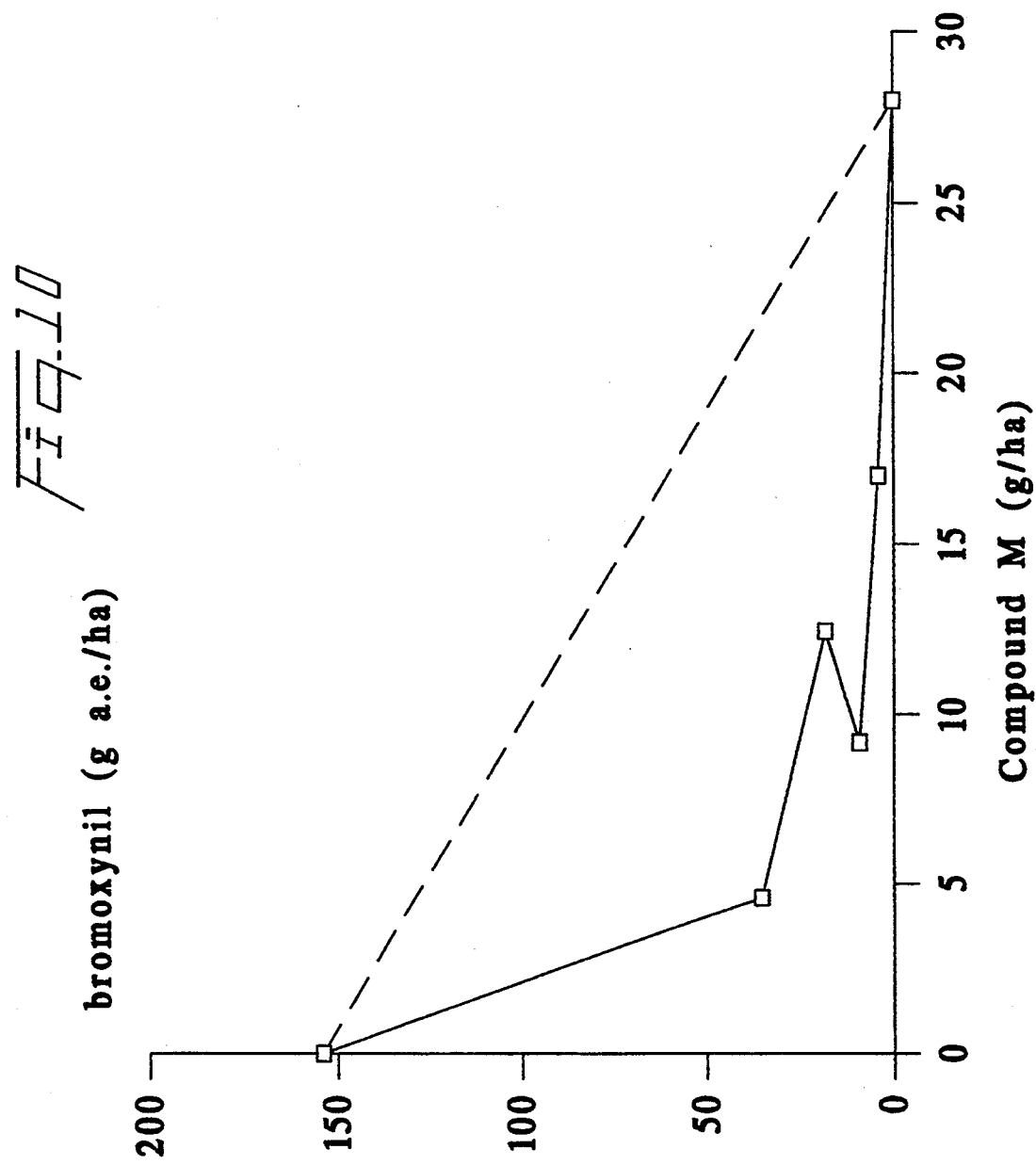
FIG. 10 is an ED50 isobole plot calculated from observed values (-□-) and a corresponding plot of expected additive values (—) for mixtures of Compound M with bromoxynil applied to *Echniochloa erus-galli* seedlings.
Figure 11:
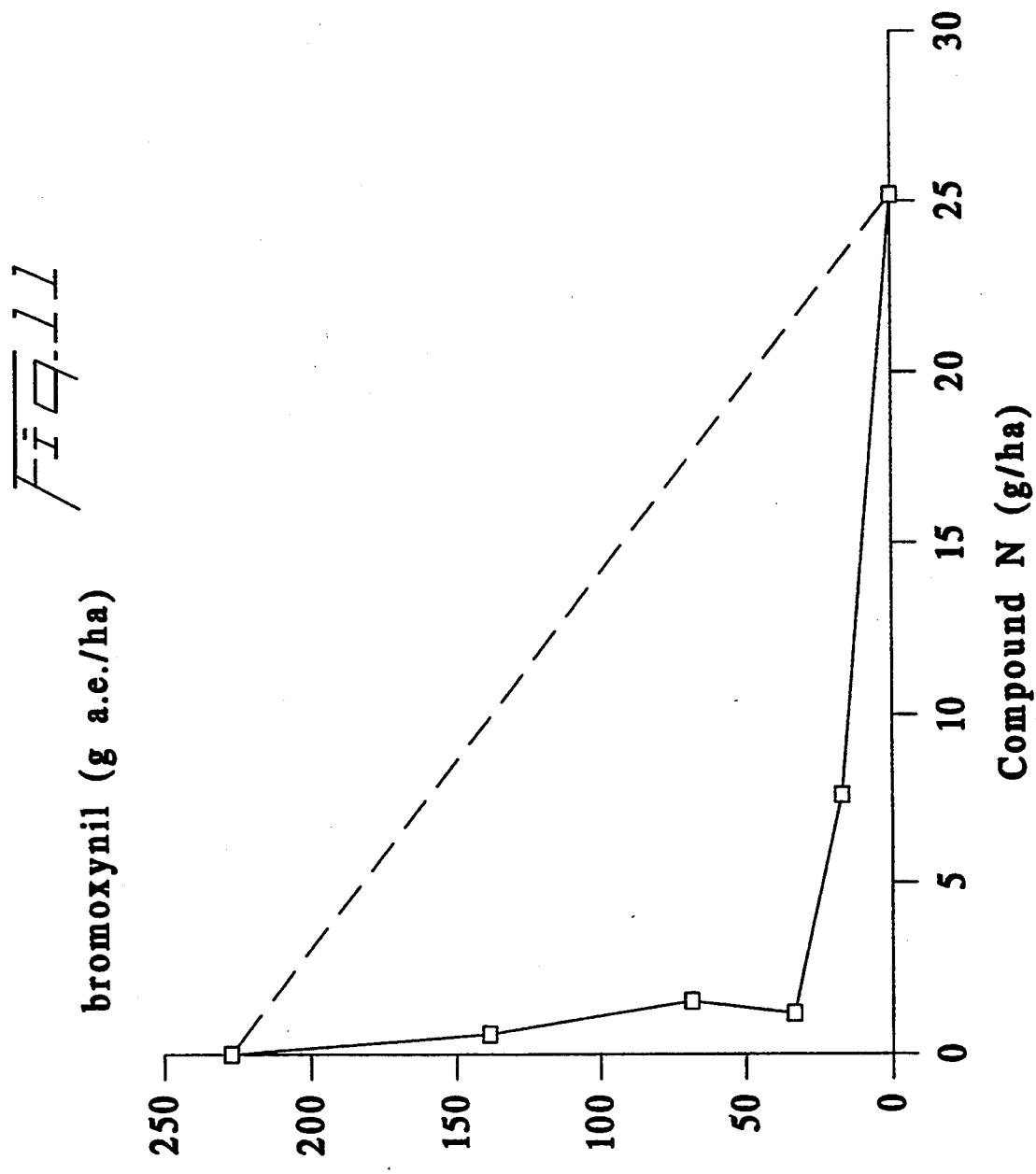
FIG. 11 is an ED50 isobole plot calculated from observed values (-□-) and a corresponding plot of expected additive values (—) for mixtures of Compound N with bromoxynil applied to *Echinochloa crus-galli* seedlings.
Figure 12:
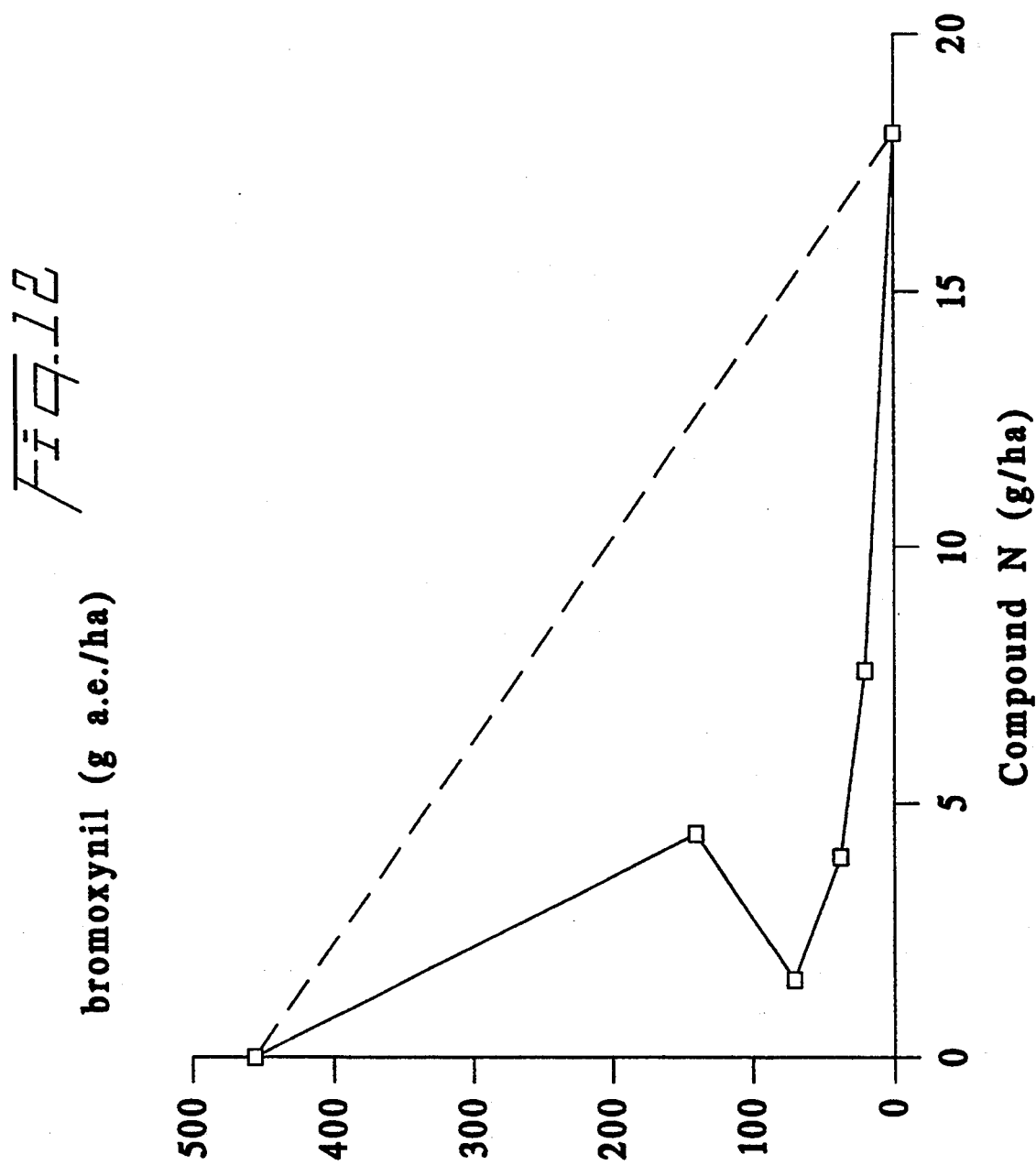
FIG. 12 is an ED50 isobole plot calculated from observed values (-□-) and a corresponding plot of expected additive values (—) for mixtures of Compound N with bromoxynil applied to *Sida spinosa* seedlings.

The isoboles produced shown hereinafter in FIGS. 4–12 are clearly either type III curves for a 'two-sided effect' (Tammes op. cit. page 75, FIG. 2) i.e. FIGS. 4 to 7 and 10 to 12, or type II curves for a 'one-sided effect' (Tammes op. cit. page 74, FIG. 1) i.e. FIGS. 8 and 9, both characteristic of synergism, thereby confirming the interpretation of the Limpel equation.

EXPERIMENT 3

A glasshouse experiment showing the biological interaction between bromoxynil and Compound D on maize.

A wide range of dose rates of technical bromoxynil phenol (9, 18, 35, 70 and 140 g/ha) and of Compound D (8, 16, 31, 63 and 125 g/ha) were applied in acetone in a spray volume of 290 l/ha to six replicate 7.5 cm square plastic pots of loam soil containing one maize plant at the three leaf growth stage.

After spraying the pots were arranged in randomised blocks in a glasshouse and subirrigated. After 11 days the plants were assessed for percentage phytotoxicity (reduction in green area compared with unsprayed plants): 0=no effect, 100=complete destruction. As can be seen in Table XI none of the treatments caused any phytotoxicity in the maize indicating that mixtures of bromoxynil and Compound D could be safely used in this crop.

TABLE XV

| Application rate (g/ha) | | % Phytotoxicity |
|---|---|---|
| Compound D | Bromoxynil | Maize |
| 8 | 0 | 0 |
| 16 | 0 | 0 |
| 31 | 0 | 0 |
| 63 | 0 | 0 |
| 125 | 0 | 0 |
| 0 | 9 | 0 |
| 0 | 18 | 0 |
| 0 | 35 | 0 |
| 0 | 70 | 0 |
| 0 | 140 | 0 |
| 4 | 4 | 0 |
| 8 | 4 | 0 |
| 16 | 4 | 0 |
| 31 | 4 | 0 |
| 63 | 4 | 0 |
| 2 | 9 | 0 |
| 4 | 9 | 0 |
| 8 | 9 | 0 |
| 16 | 9 | 0 |
| 31 | 9 | 0 |
| 1 | 18 | 0 |
| 2 | 18 | 0 |
| 4 | 18 | 0 |
| 8 | 18 | 0 |
| 16 | 18 | 0 |
| 0.5 | 35 | 0 |
| 1 | 35 | 0 |
| 2 | 35 | 0 |
| 4 | 35 | 0 |
| 8 | 35 | 0 |
| 0.5 | 70 | 0 |
| 1 | 70 | 0 |
| 2 | 70 | 0 |
| 4 | 70 | 0 |
| 8 | 70 | 0 |

According to a further feature of the present invention, there is provided a product comprising (a) bromoxynil or an agriculturally acceptable salt or ester thereof, preferably a metal or amine salt or an ester thereof with an alkanoic acid containing from 2 to 10 carbon atoms and (b) a 2-benzoylcyclohexane-1,3-dione derivative of general formula I or a salt thereof with an agriculturally acceptable base as a combined preparation for simultaneous, separate or sequential use, for example, in controlling the growth of weeds at a maize, wheat or barley crop locus.

According to a further feature of the present invention, there are provided compositions suitable for herbicidal use comprising (a) bromoxynil or an agriculturally acceptable salt or ester thereof, preferably a metal or amine salt or an ester thereof with an alkanoic acid containing from 2 to 10 carbon atoms and (b) a 2-benzoylcyclohexane-1,3-dione derivative of general formula I or a salt thereof with an agriculturally acceptable base for example in proportions of 14:1 to 1:3.33 preferably 6:1 to 1:2 and more preferably 6:1 to 1:1.25 wt/wt of acid equivalent (a) to acid equivalent (b) in association with, and preferably homogeneously dispersed in, one or more compatible herbicidally-acceptable diluents or carriers and/or surface-active agents (i.e. diluents or carriers or surface-active agents of the type generally acceptable in the art as being suitable for use in herbicidal compositions and which are compatible with bromoxynil and 2-benzoylcyclohexane-1,3-dione derivatives). The term "homogeneously dispersed" is used to include compositions in which bromoxynil and 2-benzoylcyclo-hexane-1,3-dione derivatives are dissolved in the other components. The term "herbicidal compositions" is used in a broad sense to include not only compositions which are ready for use as herbicides but also concentrates which must be diluted before use. Preferably, the compositions contain from 0.05 to 90% by weight of bromoxynil and 2-benzoylcyclohexane-1,3-dione derivative(s).

The herbicidal compositions may contain both a diluent or carrier and a surface-active (e.g. wetting, dispersing, or emulsifying) agent. Surface-active agents which may be present in herbicidal compositions of the present invention may be of the ionic or non-ionic types, for example sulphoricinoleates, products based on condensates of ethylene oxide with nonyl- or octyl-phenols, or carboxylic acid esters of anhydrosorbitols which have been rendered soluble by etherification of the free hydroxy groups by condensation with. ethylene oxide, alkali and alkaline earth metal salts or sulphuric acid esters and sulphonic acids such as dinonyl- and dioctyl-sodium sulphono-succinates and alkali and alkaline earth metal salts of high molecular weight sulphonic acid derivatives such as sodium and calcium lignosulphonates. Examples of suitable solid diluents or carriers are aluminium silicate, talc, calcined magnesia, kieselguhr, tricalcium phosphate, powdered cork, absorbent carbon black and clays such as kaolin and bentonite. The solid compositions (which may take the form of dusts, granules or wettable powders) are preferably prepared by grinding bromoxynil and the 2-benzoylcyclohexane-1,3-dione derivative with solid diluents or by impregnating the solid diluents or carriers with solutions of bromoxynil and 2-benzoyl-cyclohexane-1,3-dione derivative in volatile solvents, evaporating the solvents and, if necessary, grinding the products so as to obtain powders. Granular formulations may be prepared by absorbing bromoxynil and the 2-benzoylcyclohexane-1,3-dione derivative (dissolved in volatile solvents) onto the solid diluents or carriers in granular form and evaporating the solvents, or by granulating compositions in powder form obtained as described above. Solid herbicidal compositions, particularly wettable powders, may contain wetting or dispersing agents (for example of the types described above), which may also, when solid, serve as diluents or carriers.

Liquid compositions according to the invention may take the form of aqueous, organic or aqueous-organic solutions, suspensions and emulsions which may incorporate a surface-active agent. Suitable liquid diluents for incorporation in the liquid compositions include water, acetophenone, cyclohexanone, isophorone, toluene, xylene and mineral, animal and vegetable oils (and mixtures of these diluents). Surface-active agents, which may be present in the liquid compositions, may be ionic or non-ionic (for example of the types described above) and may, when liquid, also serve as diluents or carriers.

Wettable powders and liquid compositions in the form of concentrates may be diluted with water or other suitable diluents, for example mineral or vegetable oils, particularly in the case of liquid concentrates in which the diluent or carrier is an oil, to give compositions ready for use. When desired, liquid compositions of bromoxynil and 2-benzoylcyclohexane1,3-dione derivative may be used in the form of self-emulsifying concentrates containing the active substances dissolved in the emulsifying agents or in solvents containing emulsifying agents compatible with the active substances, the simple addition of water to such concentrates producing compositions ready for use.

Liquid concentrates in which the diluent or carrier is an oil may be used without further dilution using the electrostatic spray technique.

Herbicidal compositions according to the present invention may also contain, if desired, conventional adjuvants such as adhesives, protective colloids, thickeners, penetrating agents, stabilisers, sequestering agents, anti-caking agents, colouring agents and corrosion inhibitors. These adjuvants may also serve as carriers or diluents.

Preferred herbicidal compositions according to the present invention are aqueous suspension concentrates which comprise from 10 to 70% w/v of bromoxynil and 2-benzoylcyclohexane-1,3-dione derivative, from 2 to 10% w/v of surface-active agent, from 0.1 to 5% w/v of thickener and from 15 to 87.9% by volume of water; wettable powders which comprise from 10 to 90% w/w of bromoxynil and 2-benzoylcyclohexane-1,3-dione derivative, from 2 to 10% w/w of surface-active agent and from 8 to 88% w/w of solid diluent or carrier; liquid water soluble concentrates which comprise from 10 to 30% w/v of bromoxynil and 2-benzoylcyclohexane-1,3-dione derivative, from 5 to 25% w/v of surface-active agent and from 45 to 85% by volume of water-miscible solvent, e.g. dimethylformamide; liquid emulsifiable suspension concentrates which comprise from 10 to 70% w/v of bromoxynil and 2-benzoylcyclohexane-1,3-dione derivative, from 5 to 15% w/v of surface-active agent, from 0.1 to 5% w/v of thickener and from 10 to 84.9% by volume of organic solvent; granules which comprise from 2 to 10% w/w of bromoxynil and 2-benzoylcyclohexane-1,3-dione derivative, from 0.5 to 2% w/w of surface-active agent and from 88 to 97.5% w/w of granular carrier; and emulsifiable concentrates which comprise from 0.05 to 90% w/v, and preferably from 1 to 60% w/v, of bromoxynil and 2-benzoylcyclohexane-1,3-dione derivative, from 0.01 to 10% w/v, and preferably from 1 to 10% w/v, of surface-active agent and from 9.99 to 99.94%, and preferably from 39 to 98.99%, by volume of organic solvent.

Herbicidal compositions according to the present invention may also comprise bromoxynil and 2-benzoyl-cyclohexane-1,3-dione derivative in association with, and preferably homogeneously dispersed in, one or more other pesticidally active compounds and, if desired, one or more compatible pesticidally acceptable diluents or carriers, surface-active agents and conventional adjuvants as hereinbefore described. Examples of other pesticidally active compounds which may be included in, or used in conjunction with, the herbicidal compositions of the present invention include herbicides, for example to increase the range of weed species controlled, for example, alachlor (2-chloro-2,6-diethyl-N-methoxymethylacetanilide), bentazone (3-isopropyl-1H-2,1,3-benzothiadiazin-4(3H)-one 2,2-dioxide), cyanazine (2-chloro-4-(1-cyano-1-methylethylamino)-6-ethylamino-1,3,5-triazine), 2,4-D ((2,4-dichlorophenoxy)acetic acid), MCPA [4-chloro-2-methylphenoxyacetic acid], sulphonyl ureas e.g. nicosulfuron [2-(4',6'-dimethoxypyrimidin-2'-ylcarbamoylsulfamoyl)-N,N-dimethylnicotinamide] and CMPP (also known as mecoprop) [($\pm$)-2-(4-chloro-2-methylphenoxy)propionic acid]; insecticides for example carbamates (e.g. carbofuran), organo-phosphates (e.g. chlorpyrifos), synthetic pyrethroids (e.g. cypermethrin), acyl ureas (e.g. teflubenzuron) and *Bacillus thuringiensis*; and fungicides for example metalaxyl, carboxin and captafol. Other biologically active materials which may be included in, or used in conjunction with, the herbicidal compositions of the present invention are plant growth regulators and fertilizers containing, for example, nitrogen, potassium and phosphorus and trace elements known to be essential to successful plant life, e.g. iron, magnesium, zinc, manganese, cobalt and copper.

Pesticidally active compounds and other biologically active materials which may be included in, or used in conjunction with, the herbicidal compositions of the present invention, for example those hereinbefore mentioned, and which are acids, may, if desired, be utilized and in the form of conventional derivatives, for example alkali metal and amine salts and esters.

The compositions of the invention may be made up as an article of manufacture comprising bromoxynil and 2-benzoylcyclohexane-1,3-dione derivative of general formula I as hereinbefore defined and optionally other biologically active compounds as hereinbefore described or, as is preferred, a herbicidal composition as hereinbefore described, and preferably a herbicidal concentrate which must be diluted before use, comprising bromoxynil and 2-benzoylcyclohexane-1,3-dione derivative within a container for the aforesaid bromoxynil and 2-benzoylcyclohexane-1,3-dione derivative or a said herbicidal composition, and instructions physically associated with the aforesaid container setting out the manner in which the aforesaid bromoxynil and 2-benzoylcyclohexane-1,3-dione derivative or herbicidal composition contained therein is to be used to control the growth of weeds. The containers will normally be of the types conventionally used for the storage of chemical substances which are solids at normal ambient temperatures and herbicidal compositions, particularly in the form of concentrates, for example cans and drums of metal, which may be internally-lacquered, and plastics materials, bottles of glass and plastics materials and, when the contents of the container is a solid, for example granular herbicidal compositions, boxes, for example of cardboard, plastics materials and metal, or sacks. The containers will normally be of sufficient capacity to contain amounts of the active ingredients or herbicidal compositions sufficient to treat at least 0.5 hectare of ground to control the growth of weeds therein but will not exceed a size which is convenient for conventional methods of handling. The instructions will be physically associated with the container, for example by being printed directly thereon or on a label or tag affixed thereto. The directions will normally indicate that the contents of the container, after dilution if necessary, are to be applied to control the growth of weeds at rates of application from 2 g to 350 g a.e. of bromoxynil and from 0.5 g to 500 g a.e. of 2-benzoylcyclohexane-1,3-dione derivative per hectare in the manner and for the purposes hereinbefore described.

The following Examples illustrate herbicidal compositions according to the present invention and herbicidal compositions suitable for use in the method for controlling the growth of weeds according to the present invention.

EXAMPLE 1

A water soluble powder was made from:

| | | |
|---|---|---|
| Compound A | 60% w/w | |
| Sodium carbonate | 25% w/w | |
| Atlox 4901 | 3.75% w/w | |
| Sodium metaphosphate | 4% w/w | |
| Precipitated silica | 7.25% w/w | | by using all the ingredients together and milling in a hammer mill.

EXAMPLE 2

A 14:1 mixture was formed by tank mixing 1.6 liters of a commercially available emulsifiable concentrate formulation containing 225 g/l bromoxynil phenol equivalent as the octanoate ester with 42 g of the composition of Example 1 in a volume of 200 liters of 0.2% v/v nonylphenol ethylene oxide condensate solution in water. The resulting spray fluid was applied to one hectare of maize to control *Amaranthus retroflexus, Chenopodium album, Solanum nigrum* and *Xanthium pennsylvanicum*.

EXAMPLE 3

A 1:3.33 mixture was formed by tank mixing 667 ml of a commercially available emulsifiable concentrate formulation containing 225 g/l w/v bromoxynil phenol equivalent as the octanoate ester with 833 g of the composition of Example 1 in a volume of 200 liters 0.2% v/v nonylphenol ethylene oxide condensate solution in water. The resulting spray fluid was applied to one hectare of maize to control *Bidens pilosa, Eleusine indica, Echinochloa crus-galli* and *Digitaria sanguinalis*.

In the mixed formulations in the Examples hereinbefore, the 2-benzoylcyclohexane-1,3-dione derivative may be replaced by other 2-benzoylcyclohexane-1,3-dione derivatives of general formula I.

The processes described in European Patent Publications Nos. 135191, 137963 and 186118 may be used to prepare the compounds of general formula I.

Intermediate cyclohexane-1,3-diones may be prepared in a similar manner to that described in West German Patent Publication No. 2412313 and European Patent Publication No. 61669.

The following Reference Example illustrates the preparation of compounds of general formula I.

REFERENCE EXAMPLE 1

Compound G

A solution of 4-methylsulphonyl-2-nitrobenzoyl chloride (9.62 g) in dry dichloromethane (50 ml) was added to a stirred solution of triethylamine (5.6 ml) and 5,5-dimethylcyclohexane-1,3-dione (5 g) in dry dichloromethane (70 ml) during 30 minutes and the reaction mixture stirred at ambient temperature for 4 hours. Triethylamine (15.3 ml) and acetone cyanohydrin (0.5 ml) were added successively and the reaction mixture stirred at ambient temperature for 18 hours. The reaction mixture was washed successively with 2N hydrochloric acid (2×50 ml) and water (2×50 ml), dried over magnesium sulphate and evaporated under reduced pressure to give a yellow glass which was recrystallised from methanol (20 ml) to give 2-(4-methylsulphonyl-2-nitrobenzoyl)-5,5-dimethylcyclohexane-1,3-dione (6.4 g), m.p. 156.5°–158° C., as a yellow crystalline solid.

By proceeding in a similar manner to that described above the following compounds were prepared:-

| Compound | m.p./°C. |
|---|---|
| A | 140–141.5 |
| B | 142–143.5 |
| C | 131–133 |
| D | 139–140 |
| E | 140–142 |
| F | — |

-continued

| Compound | m.p./°C |
|---|---|
| H | 112–114 |
| H | 112–114 |
| I | 86–87 |
| J | 133–135 |
| K | 137–138 |
| L | 115–117 |
| M | — |
| N | 172–174 |

What is claimed is:

1. A method for controlling the growth of weeds at a locus which comprises applying to the locus a synergistic herbicidally effective amount of:
   (a) bromoxynil or an agriculturally acceptable salt or ester thereof; and
   (b) a 2-benzoylcyclohexane-1,3-dione of the formula

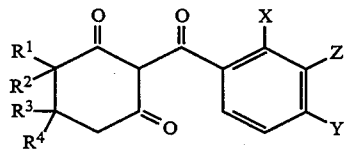

wherein:
(i) Z represents the hydrogen atom;
   $R^1$ and $R^2$, which may be the same or different, each represents the hydrogen atom or the methyl group;
   $R^3$ and $R^4$, which may be the same or different, each represents the hydrogen atom or the methyl group;
   X represents the chlorine atom or the nitro group;
   Y represents the methylsulphonyl or trifluoromethyl group; or
(ii) Z represents the chlorine atom;
   $R^1$, $R^2$, $R^3$ and $R^4$ each represent the hydrogen atom;
   X represents the chlorine atom; and
   Y represents the methylsulphonyl group; or a salt thereof with an agriculturally acceptable base.

2. The method according to claim 1 wherein, in the 2-benzoylcyclohexane-1,3-dione of formula (I), Z represents the hydrogen atom and $R^3$ and $R^4$ both represent hydrogen atoms or both represent methyl groups.

3. The method according to claim 1 wherein, in the 2-benzoylcyclohexane-1,3-dione of formula (I), $R^1$ and $R^2$ both represent hydrogen atoms or both represent methyl groups and $R^3$ and $R^4$ both represent hydrogen atoms or both represent methyl groups.

4. The method according to claim 2 wherein, in the 2-benzoylcyclohexane-1,3-dione of formula (I), $R^1$ and $R^2$ both represent hydrogen atoms or both represent methyl groups.

5. The method according to claim 1 wherein from about 2 g to about 350 g a.e./ha of bromoxynil and from about 0.5 g to about 500 g a.e./ha of a 2-benzoylcyclohexane-1,3-dione of formula (I) are applied.

6. The method according to claim 2 wherein from about 2 g to about 350 g a.e./ha of bromoxynil and from about 0.5 g to about 500 g a.e./ha of a 2-benzoylcyclohexane-1,3-dione of formula (I) are applied.

7. The method according to claim 3 wherein from about 2 g to about 350 g a.e./ha of bromoxynil and from about 0.5 g to about 500 g a.e./ha of a 2-benzoylcyclohexane-1,3-dione of formula (I) are applied.

8. The method according to claim 4 wherein from about 2 g to about 350 g a.e./ha of bromoxynil and from about 0.5 g to about 500 g a.e./ha of a 2-benzoylcyclohexane-1,3-dione of formula (I) are applied.

9. The method according to claim 5 wherein from about 150 g to about 350 g a.e./ha of bromoxynil and from about 25 g to about 500 g a.e./ha of a 2-benzoylcyclohexane-1,3-dione of formula (I) are applied.

10. The method according to claim 6 wherein from about 150 g to about 350 g a.e./ha of bromoxynil and from about 25 g to about 500 g a.e./ha of 2-benzoylcyclohexane-1,3-dione of formula (I) are applied.

11. The method according to claim 7 wherein from about 150 g to about 350 g a.e./ha of bromoxynil and from about 25 g to about 500 g a.e./ha of a 2-benzoylcyclohexane-1,3-dione of formula (I) are applied.

12. The method according to claim 8 wherein from about 150 g to about 350 g a.e./ha of bromoxynil and from about 25 g to about 500 g a.e./ha of a 2-benzoylcyclohexane-1,3-dione of formula (I) are applied.

13. The method according to claim 9 wherein from about 150 g to about 350 g a.e./ha of bromoxynil and from about 50 g to about 400 g a.e./ha of a 2-benzoylcyclohexane-1,3-dione of formula (I) are applied.

14. The method according to claim 10 wherein from about 150 g to about 350 g a.e./ha of bromoxynil and from about 50 g to about 400 g a.e./ha of a 2-benzoylcyclohexane-1,3-dione of formula (I) are applied.

15. The method according to claim 11 wherein from about 150 g to about 350 g a.e./ha of bromoxynil and from about 50 g to about 400 g a.e./ha of a 2-benzoylcyclohexane-1,3-dione of formula (I) are applied.

16. The method according to claim 12 wherein from about 150 g to about 350 g a.e./ha of bromoxynil and from about 50 g to about 400 g a.e./ha of a 2-benzoylcyclohexane-1,3-dione of formula (I) are applied.

17. The method according to claim 13 wherein from about 200 g to about 300 g a.e./ha of bromoxynil and from about 50 g to about 250 g a.e./ha of a 2-benzoylcyclohexane-1,3-dione of formula (I) are applied.

18. The method according to claim 14 wherein from about 200 g to about 300 g a.e./ha of bromoxynil and from about 50 to about 250 g a.e./ha of a 2-benzoylcyclohexane-1,3-dione of formula (I) are applied.

19. The method according to claim 15 wherein from about 200 g to about 300 g a.e./ha of bromoxynil and from about 50 to about 250 g a.e./ha of a 2-benzoylcyclohexane-1,3-dione of formula (I) are applied.

20. The method according to claim 16 wherein from about 200 g to about 300 g a.e./ha of bromoxynil and from about 50 to about 250 g a.e./ha of a 2-benzoylcyclohexane-1,3-dione of formula (I) are applied.

21. The method according to claim 1 wherein the locus is a maize, wheat or barley crop-growing area.

22. The method according to claim 2 wherein the locus is a maize, wheat or barley crop-growing area.

23. The method according to claim 3 wherein the locus is a maize, wheat or barley crop-growing area.

24. The method according to claim 4 wherein the locus is a maize, wheat or barley crop-growing area.

25. A herbicidal combination comprising a synergistic herbicidally effective amount of:
   (a) bromoxynil or an agriculturally acceptable salt or ester thereof; and
   (b) a 2-benzoylcyclohexane-1,3-dione of the formula

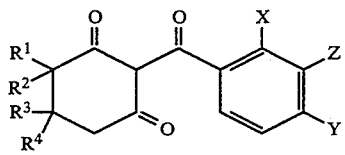

wherein:
(i) Z represents the hydrogen atom;
R$^1$ and R$^2$ which may be the same or different, each represents the hydrogen atom or the methyl group;
R$^3$ and R$^4$, which may be the same or different, each represents the hydrogen atom or the methyl group;
X represents the chlorine atom or the nitro group;
Y represents the methylsulphonyl or trifluoromethyl group; or
(ii) Z represents the chlorine atom;
R$^1$, R$^2$, R$^3$ and R$^4$ each represent the hydrogen atom;
X represents the chlorine atom; and
Y represents the methylsulphonyl group; or a salt thereof with an agriculturally acceptable base.

26. The herbicidal combination according to claim 25 wherein, in the 2-benzoylcyclohexane-1,3-dione of formula (I), Z represents the hydrogen atom and R$^3$ and R$^4$ both represent hydrogen atoms or both represent methyl groups.

27. The herbicidal combination according to claim 25 wherein, in the 2-benzoylcyclohexane-1,3-dione of formula (I), R$^1$ and R$^2$ both represent hydrogen atoms or both represent methyl groups and R$^3$ and R$^4$ both represent hydrogen atoms or both represent methyl groups.

28. The herbicidal combination according to claim 26 wherein, in the 2-benzoylcyclohexane-1,3-dione of formula (I), R$^1$ and R$^2$ both represent hydrogen atoms or both represent methyl groups.

29. A herbicidal composition comprising:
(1) a herbicidally effective amount synergistic of:
(a) bromoxynil or an agriculturally acceptable salt or ester thereof; and
(b) a 2-benzoylcyclohexane-1,3-dione of the formula

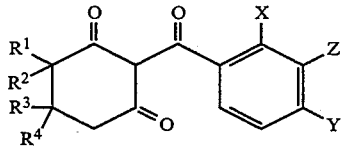

wherein:
(i) Z represents the hydrogen atom;
R$^1$ and R$^2$, which may be the same or different, each represents the hydrogen atom or the methyl group;
R$^3$ and R$^4$, which may be the same or different, each represents the hydrogen atom or the methyl group;
X represents the chlorine atom or the nitro group;
Y represents the methylsulphonyl or trifluoromethyl group; or
(ii) Z represents the chlorine atom;
R$^1$, R$^2$, R$^3$ and R$^4$ each represents the hydrogen atom;
X represents the chlorine atom; and
Y represents the methylsulphonyl group; or a salt thereof with an agriculturally acceptable base; and
(2) at least one member selected from the group consisting of a herbicidally acceptable carrier and a herbicidally acceptable surface active agent.

30. The herbicidal composition according to claim 29 wherein, in the 2-benzoylcyclohexane-1,3-dione of formula (I), Z represents the hydrogen atom and R$^3$ and R$^4$ both represent hydrogen atoms or both represent methyl groups.

31. The herbicidal composition according to claim 29 wherein, in the 2-benzoylcyclohexane-1,3-dione of formula (I), R$^1$ and R$^2$ both represent hydrogen atoms or both represent methyl groups and R$^3$ and R$^4$ both represent hydrogen atoms or both represent methyl groups.

32. The herbicidal composition according to claim 30 wherein, in the 2-benzoylcyclohexane-1,3-dione of formula (I), R$^1$ and R$^2$ both represent hydrogen atoms or both represent methyl groups.

33. The herbicidal composition according to claim 29 wherein the proportion of bromoxynil (a.e.): 2-benzoylcyclohexane-1,3-dione of formula (I) (a.e.) is from about 14:1 to about 1:3.33 wt/wt.

34. The herbicidal composition according to claim 30 wherein the proportion of bromoxynil (a.e.): 2-benzoylcyclohexane-1,3-dione of formula (I) (a.e.) is from about 14:1 to about 1:3.33 wt/wt.

35. The herbicidal composition according to claim 31 wherein the proportion of bromoxynil (a.e.): 2-benzoylcyclohexane-1,3-dione of formula (I) (a.e.) is from about 14:1 to about 1:3.33 wt/wt.

36. The herbicidal composition according to claim 32 wherein the proportion of bromoxynil (a.e.): 2-benzoylcyclohexane-1,3-dione of formula (I) (a.e.) is from about 14:1 to about 1:3.33 wt/wt.

37. The herbicidal composition according to claim 33 wherein the proportion of bromoxynil (a.e.): 2-benzoylcyclohexane-1,3-dione of formula (I) (a.e.) is from about 6:1 to about 1:1.25 wt/wt.

38. The herbicidal composition according to claim 34 wherein the proportion of bromoxynil (a.e.): 2-benzoylcyclohexane-1,3-dione of formula (I) (a.e.) is from about 6:1 to about 1:1.25 wt/wt.

39. The herbicidal composition according to claim 35 wherein the proportion of bromoxynil (a.e.): 2-benzoylcyclohexane-1,3-dione of formula (I) (a.e.) is from about 6.1 to about 1:1.25 wt/wt.

40. The herbicidal composition according to claim 36 wherein the proportion of bromoxynil (a.e.): 2-benzoylcyclohexane-1,3-dione of formula (I) (a.e.) is from about 6:1 to about 1:1.25 wt/wt.

41. A method for controlling the growth of weeds at a locus which comprises applying to the locus a synergistic herbicidally effective amount of:
(a) bromoxynil or an agriculturally acceptable salt or ester thereof; and
(b) 2-(2-chloro-4-methylsulphonylbenzoyl)cyclohexane- 1,3-dione or a salt thereof with an agriculturally acceptable base.

42. A herbicidal combination comprising a synergistic herbicidally effective amount of:
(a) bromoxynil or an agriculturally acceptable salt or ester thereof; and
(b) 2-(2-chloro-4-methylsulphonylbenzoyl)cyclohexane- 1,3-dione or a salt thereof with an agriculturally acceptable base.

43. A herbicidal composition comprising:

(1) a synergistic herbicidally effective amount of:
   (a) bromoxynil or an agriculturally acceptable salt or ester thereof; and
   (b) 2-(2-chloro-4-methylsulphonylbenzoyl)cyclohexane-1,3-dione or a salt thereof with an agriculturally acceptable base; and
(2) at least one member selected from the group consisting of a herbicidally acceptable carrier and a herbicidally acceptable surface active agent.

* * * * *